United States Patent [19]
Wiedenhoefer

[11] Patent Number: 5,832,422
[45] Date of Patent: Nov. 3, 1998

[54] MEASURING DEVICE

[76] Inventor: Curt Wiedenhoefer, 44128 Lakeview Dr., El Macero, Calif. 95618

[21] Appl. No.: 420,552

[22] Filed: Apr. 11, 1995

[51] Int. Cl.[6] .............................. G09G 5/00; G01B 11/00
[52] U.S. Cl. .............................. 702/154; 33/1 D; 33/1 N; 345/162; 345/169; 702/161
[58] Field of Search .................................. 364/561, 562, 364/550; 33/1 D, 1 N, 1 S, 700, 706, 783, 784; 345/157, 160, 162, 169; 702/150, 151, 154, 161

[56] References Cited

U.S. PATENT DOCUMENTS

| | | | |
|---|---|---|---|
| 4,158,229 | 6/1979 | Woo, Jr. et al. | 364/562 |
| 4,257,107 | 3/1981 | Heymsfield et al. | 364/562 X |
| 4,520,674 | 6/1985 | Canada et al. | |
| 5,410,494 | 4/1995 | Hashimoto et al. | 345/173 |

OTHER PUBLICATIONS

"Measuring Range Of Motion With The Ortho Ranger II Inclinometer" published by Medical Instrument Technology, Inc.; copyright 1989.
"Medical Instruments Technology" by M.I.Tech, Inc. (no date).
Order Form from M.I.Technologies (no date).
Flyer from Ortho–Graphics (no date).
"Product Overview" from Ortho–Graphics (no date).
"Image Capture System" from Ortho–Graphics, Inc. (no date).
"Orthoscan (TM) Features" from Ortho–Graphics (no date).
"Orthoplan (TM)" from Ortho–Graphics including last page.
"Computer Assisted Preoperative Planning Available for Office Computers" by Peter M. Stevens, M.D. (no date).
"Researchmetrics (TM) Features" from Ortho–Graphics (no date) (6 pages).
"Orthoview (TM)" newsletter from Ortho–Graphics, Inc., Nov. 1993.

Primary Examiner—William A. Cuchlinski, Jr.
Assistant Examiner—Edward J. Pipala
Attorney, Agent, or Firm—Peter Peckarsky

[57] ABSTRACT

A measuring device capable of being used by physicians, veterinarians, and surgeons either pre-operatively, intraoperatively, or post-operatively to determine the actual size of objects shown in images made by x-rays (and other imaging techniques). The measuring device is electronic and can also be used to measure the angle between two objects whose images are shown. The measuring device can also be used to determine the proper size and shape of implants to be surgically implanted in a living body. The device can also be used to determine the proper size and shape for templates to be used to select an implant to be surgically implanted in a living body.

41 Claims, 19 Drawing Sheets

Figure 9

Functional Specifications
Flowcharts of Excaliper's modes and functions

HOW TO READ THE FLOW CHARTS:

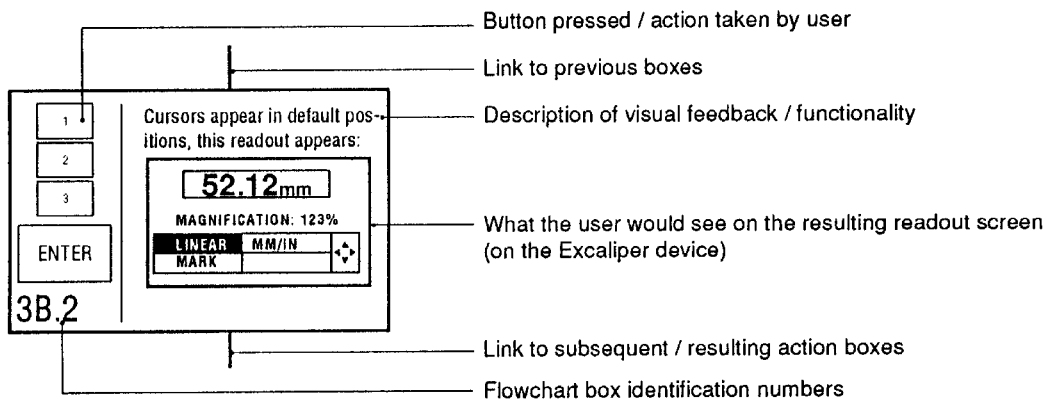

- Button pressed / action taken by user
- Link to previous boxes
- Description of visual feedback / functionality
- What the user would see on the resulting readout screen (on the Excaliper device)
- Link to subsequent / resulting action boxes
- Flowchart box identification numbers

THE READOUT SCREEN:

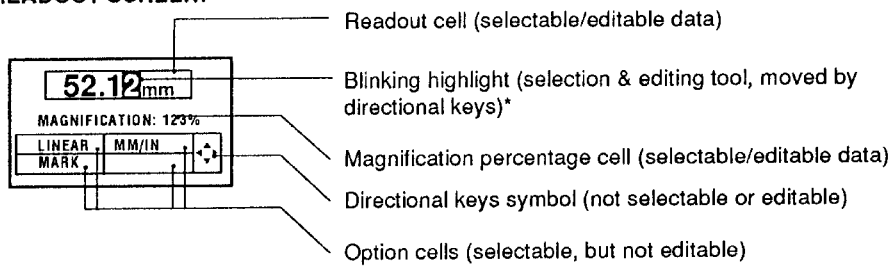

- Readout cell (selectable/editable data)
- Blinking highlight (selection & editing tool, moved by directional keys)*
- Magnification percentage cell (selectable/editable data)
- Directional keys symbol (not selectable or editable)
- Option cells (selectable, but not editable)

*Note: the blinking highlight would work the same way as cursors in text editing programs: as user types a letter, the cursor simultaneously bumps to the next letter/character space. Highlight only blinks in the editable data cells, i.e., readout cell, and magnification cell as well as name and telephone number cells.

GLOSSARY & KEY TO SYMBOLS:

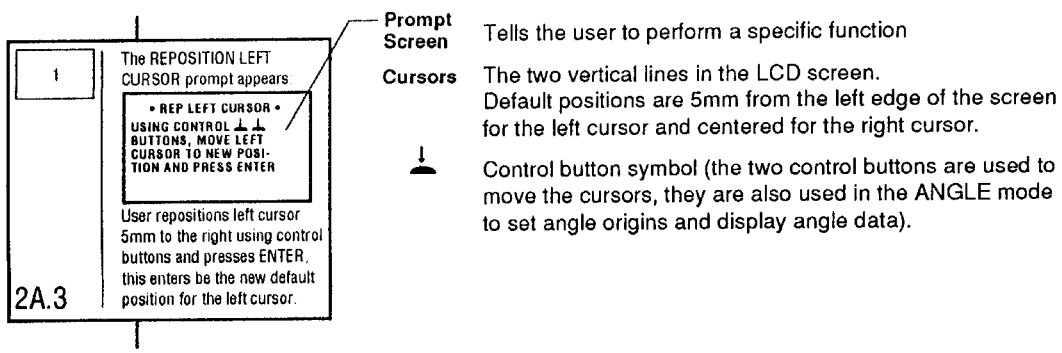

Prompt Screen — Tells the user to perform a specific function

Cursors — The two vertical lines in the LCD screen. Default positions are 5mm from the left edge of the screen for the left cursor and centered for the right cursor.

Control button symbol (the two control buttons are used to move the cursors, they are also used in the ANGLE mode to set angle origins and display angle data).

Set-Up Mode Functions

Set-Up Mode Functions, continued...

Caliper Mode Functions

Caliper Mode Functions, continued...

Figure 11C
Caliper Mode Functions, continued...

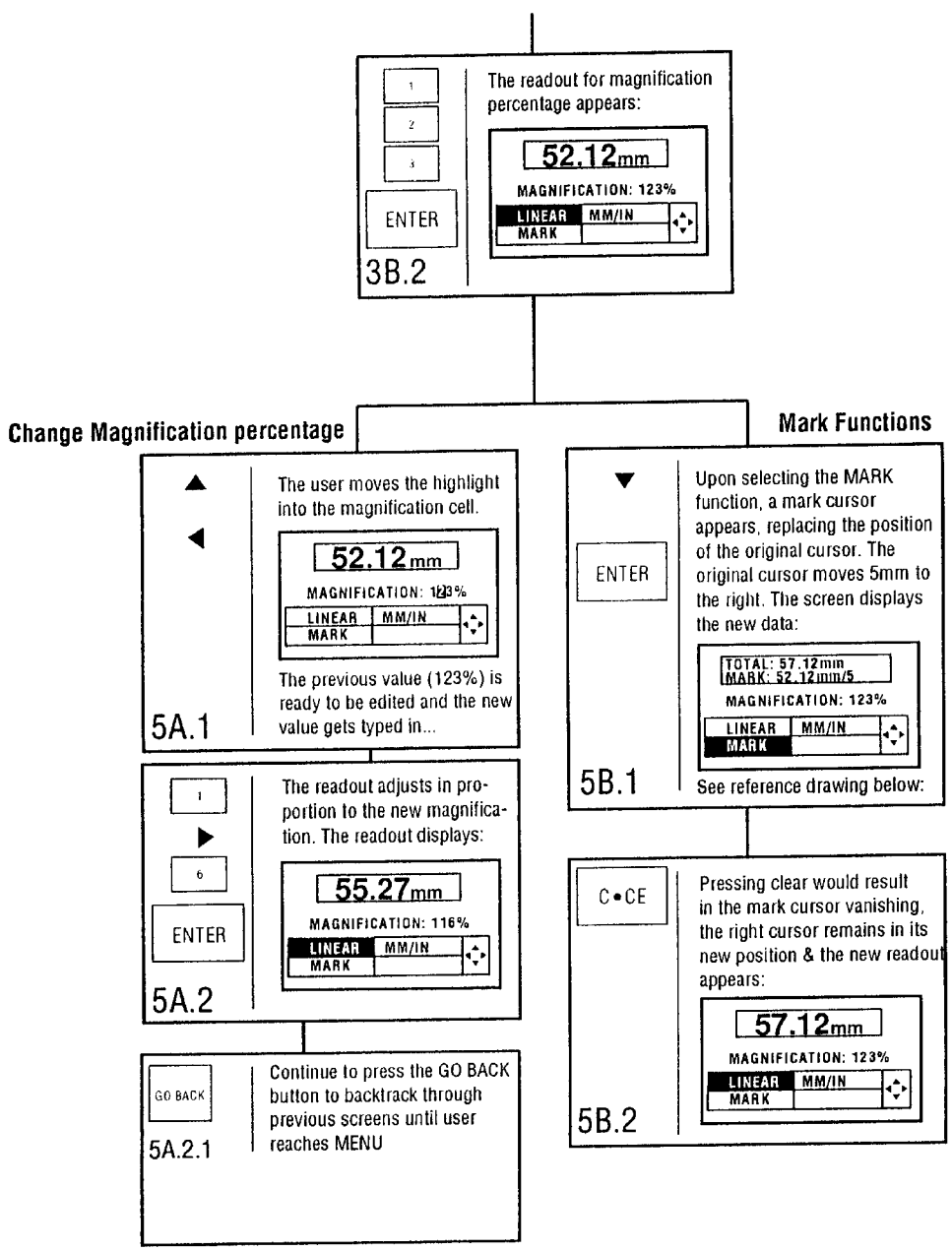

Note: when changing previously entered data, the user positions the highlight (using directional keys ◆) and either types over old data, number by number, or, the user may delete the entire contents of a cell by positioning the highlight anywhere within the cell and pressing C•CE.

Note: both the magnification % value cell and the mm value cell can be cleared (C•CE), but both cells cannot be deleted/empty at the same time.

Rule: first clear and input the data values in one and press ENTER, then clear and input the data values in the next and press ENTER.

Caliper Mode Functions, continued...

Caliper Mode Functions, continued...

Angle and Goniometer Functions

Calculator Mode Functions

To return to another mode the user presses FUNCTION for the menu.

MEASURING DEVICE

FIELD OF THE INVENTION

This invention relates to applications in which an electronic device is used to measure images of objects to provide an accurate measurement of the actual objects whose images are portrayed. This invention also relates to applications in which an electronic device is used to provide an accurate measurement of angles.

BACKGROUND OF THE INVENTION

Presently, it is difficult to measure exactly the actual distance represented by a distance on a radiograph (or, colloquially, X-ray). This is because of parallax and other causes which result in the length of an image on the developed radiograph not being equal to the actual length of the item or object (e.g., a patient's arm) being measured or shown on the developed X-ray.

For example, the magnification of x-ray images causes difficulty in diagnosis and treatment of structural conditions encountered in orthopaedics and other medical fields. The process of converting the x-ray image to actual size consumes valuable operating room time and physician time (preoperative and intraoperative) and introduces the possibility of error into measurements. This error can adversely affect the quality of medical services provided and the actual result experienced by the patient. Further, such measurement errors could be the source of professional malpractice liability for physicians and others involved in treating a patient.

In many cases, the magnification factor (the amount by which the actual object size has been enlarged) is affected by the soft tissues surrounding the bone which tissues may determine the distance between the bone and the radiograph cassette. On a radiograph the ratio of the image size to the actual object size may be a number different than 1.0. The magnification factor may vary from patient to patient due to anatomical differences. As a result, the magnification factor is an unknown variable (until determined by measurement). In computer-generated images (such as computerized axial tomography or CAT-scans) the images may be less than, equal to, or greater than the actual size of the object portrayed because in the computer processing of the information, the size of the images may have been reduced, maintained constant, or enlarged from their actual size. In the case of objects which have been reduced in size, it is necessary to determine a minimization factor (the amount by which the actual object size has been reduced) to determine the actual size of the structure depicted on the developed scan from a measurement of the image on the developed scan. Each x-ray or scan will typically have a different magnification or minimization factor. Given the above discussion and understanding, the factor will be referred to below as a magnification factor unless the context requires otherwise.

Historically, the problem of an unknown magnification factor has been solved by placing a radio-opaque (impenetrable by x-rays) marker of known dimensions in the same plane as the bone being measured. This radio-opaque marker, having known dimensions, can be measured on the developed radiograph. Thus, the magnification factor can be calculated by dividing the length of an image measured from the developed radiograph by the known length of the object. These calculations are still challenging and time consuming due to the potentially large number of measurements and related mathematical conversions which may be required for a given medical procedure or series of procedures. Standard transparent rulers and magnified overlays are used by physicians to assist in the task of accurately measuring the structures of interest. However, there is still a substantial amount of estimating and guess work involved in the measurement process.

Ortho-Graphics, Inc., 807 East South Temple, Suite 330, Salt Lake City, Utah 84102 sells a family of computer systems for managing and reporting orthopaedic clinical data for outcomes analysis, medical practice, research, and education. For image processing and analysis, a graphical device (for example, a digitizing tablet), a video input device (for example, a video camera), or a radiograph scanner is used to input the information from a radiograph or scan into a microcomputer. The medical image data may then be manipulated by the computer for outcomes analysis, enhancement, annotation, storage/retrieval, communication, and planning of surgical procedures including implant selection and tracking. The Ortho-Graphics products do not appear to be hand-held. Utilization of the Ortho-Graphics products requires the user to digitize a radiograph or scan, to put the digitized data into a computer, and to make measurements from a computer screen.

Devices called the Ortho Ranger II, Ortho III, and Ortho Max offered by M.I. Tech, Inc., or Medical Instrument Technology Inc., or M.I. Technologies, 4239 S. Atlantic Avenue, Daytona Beach, Fla., can be used to measure angles on an X-ray. These devices (such as the Ortho Ranger II) can be used with an attachment to measure distances on an X-ray film. However, these devices (such as the Ortho Ranger II) do not measure distances digitally. Further, these devices (such as the Ortho Ranger II) do not adjust for magnification/minimization problems.

Various features of the Ortho Ranger are mentioned in a 154 page booklet dated in 1989 (entitled "Measuring Range of Motion With The Ortho Ranger II Inclinometer—An Illustrated Guide referring to M.I. Tech, Inc., and Medical Instrument Technology, Inc., at the address stated above) and in a double-sided single page brochure (entitled "Now . . . as Never Before Accurate Measurement of Range of Motion Ortho Ranger referring to M.I. Technologies at the address stated above). The brochure is undated but refers to the 154 page booklet. The Ortho III and Ortho Max are referred to in an undated double-sided single page brochure from M.I. Tech Inc., at the address stated above. The following information is being submitted with respect to this patent application along with an Information Disclosure Statement:

1. A copy of a 154 page booklet entitled "Measuring Range of Motion With The Ortho Ranger II Inclinometer—An Illustrated Guide (published by Medical Instrument Technology, Inc., 4239 S. Atlantic Ave., Daytona Beach, Fla. 32116);

2. A copy of a double-sided flyer entitled "Medical Instruments Technology" from M.I. Tech, Inc., 4239 S. Atlantic Ave., Daytona Beach, Fla. 32116;

3. A copy of a double-sided order form from M.I. Technologies, P.O. Box 7471, Daytona Beach, Fla. 32116;

4. A double-sided flyer from Ortho-Graphics, Inc., 807 South Temple Street, Suite 330, Salt Lake City, Utah 84102;

5. A single page entitled "Product Overview" from Ortho-Graphics, Inc.;

6. Four (4) pages entitled "Image Capture System" from Ortho-Graphics, Inc.;

7. Three (3) pages entitled "Orthoscan (TM) Features" from Ortho-Graphics, Inc.;

8. Six (6) pages entitled "Orthoplan (TM)" from Ortho-Graphics, Inc.;

9. Six (6) pages entitled "Researchmetrics (TM) Features" from Ortho-Graphics, Inc.; and, 10. A six (6) page newsletter entitled "Orthoview" from Ortho-Graphics, Inc.

SUMMARY OF THE INVENTION

One aim of the present invention (the Electronic X-Ray Caliper (EXCALIPER™)) developed by the inventor is to resolve many of the problems related to magnification/minimization factor calculations on developed radiographs and images made using computerized axial tomography (CAT scans), positron emission tomography (PET scans), magnetic resonance imaging (MRI) and other techniques which may be used now and in the future.

Another aim of the present invention is to provide in EXCALIPER™ (in the preferred embodiment) a hand-held measuring device designed to fit in the coat pocket of the physician, technician, nurse, or bioengineer which will provide accurate measurement of the actual size of anatomical structures portrayed in radiographs or scans by comparing the known value of a dimension of a radio-opaque marker shown on a radiograph or a scale shown on a scan with the measured value of the same dimension of the radio-opaque marker or scale as measured directly from the radiograph or scan.

Another aim of the present invention is to allow its user to calibrate the device to the radiograph magnification factor. By using the EXCALIPER product, physicians and surgeons can quickly and accurately measure actual sizes of bones, organs, and other objects which have been converted into an image which image does not have dimensions with the same measurement as the actual object.

Another aim of the present invention is to provide a device which can be used to gather information from a radiograph or bone scan which information is put into a computer and used to produce a template for use in selecting an appropriate size of implant.

Another aim of the present invention is to provide a hand-held electronic device which can be used to assist in patient implant matching which involves selecting an implant with appropriate material, cost, and design.

In addition to pre-operative applications, another aim of the present invention is to provide a device which can also be used intraoperatively. During an orthopaedic surgical procedure, the surgeon is presented with situations that require decisions. The surgeon must gather information from various instruments and equipment. One of the most useful instruments is an image intensifier which makes use of a moveable arm on an x-ray machine and a video monitor to allow the surgeon intermittently or continuously to view the bone through the surrounding soft tissues. In intraoperative situations, the EXCALIPER can be calibrated to the image projected by the image intensifier on the video monitor by placing in the EXCALIPER's memory the known dimensions of the available or implanted hardware or instruments being used in the surgical case which hardware or instruments have an image also appearing on the video monitor. The surgeon can then make measurements of the various dimensions of the bones and/or deformities of interest. Use of the EXCALIPER intraoperatively can give the surgeon better information on a more timely basis than before the invention of the EXCALIPER. Providing better (more accurate) information more quickly than before will help the surgeon make key decisions and will also help the surgeon to make better use of his time, his staff's time, and operating room time. Further, if operations are completed more quickly than before, the risk to the patient should be reduced because the patient will not have to be anesthetized as long as before the invention of the EXCALIPER. Use of the EXCALIPER also gives the surgeon an efficient, alternative means of more accurately and quickly determining the proper size of surgical plates, surgical bone screws, and surgical nails to be used in view of the patient's anatomy. The EXCALIPER may also be used post-operatively by calibrating the EXCALIPER to the size of radio-opaque implants which have been implanted and then making appropriate measurements from images of the implants in the patient.

Another aim of the present invention is to provide a means to establish a benchmark in the immediate post-operative period with respect to initial placement of an implanted device. The information obtained in the immediate post-operative period could then be stored in a computer or personal computer and used as a benchmark for future analysis of radiographic changes or changes in other images with respect to radiolucency, osteolysis, and heterotopic bone which analysis will assist in implant tracking.

Another aim of the present invention is to provide for applications in topography, aerial reconnaissance, map-making, map-reading, and other fields in which it is necessary or useful to know the exact size of an object whose image is portrayed with an image size not equal to the actual object size.

Another aim of the present invention is to provide a means by which the angle between two items (for example, but not by way of limitation, two bones) can be measured by a single hand-held electronic device without an external attachment or attachments.

Another aim of the present invention is to provide a means for making anatomical measurements calibrated to a specific radiograph magnification factor which measurements may then be transmitted to a computer for storage and in some cases further analysis (pre-operatively or post-operatively) and/or generation of templates for implants.

Another aim of the present invention is to provide a means for making measurements and ratio measurements on a two dimensional surface while looking through a liquid crystal device or other clear screen on which cursors used in measurement may be generated.

Another aim of the present invention is to provide a hand-held electronic device which may be used in conjunction with a template generator to produce templates for use in orthopaedic surgery.

Another aim of the present invention is to provide a hand-held electronic device which may be used to acquire relevant anatomical and other information and to select an appropriate orthopaedic or other implant for use in human or animal bodies.

Another aim of the present invention is to provide a handheld device electronic device which may be used to track the progress of an implant in a human or animal body.

These aims are satisfied by a device with the capability to provide accurate measurement of the actual size of objects shown as radiographic or other images and the capability of measuring the angle between two objects (for example, two bones meeting at a joint) as shown and described in the accompanying drawings and description of the preferred embodiment and the claims.

These and further operational and structural characteristics of the invention will be more evident from the detailed description given hereinafter with reference to the figures of the accompanying drawings which illustrate one preferred embodiment by way of non-limiting examples.

BRIEF DESCRIPTION OF THE DRAWINGS

FIG. 9 shows an explanation of the nomenclature used in FIGS. 11A–13.

FIG. 11C shows the third of five flow charts explaining the operation of the Caliper Mode of the device.

DESCRIPTION OF THE PREFERRED EMBODIMENT

Figure 1:
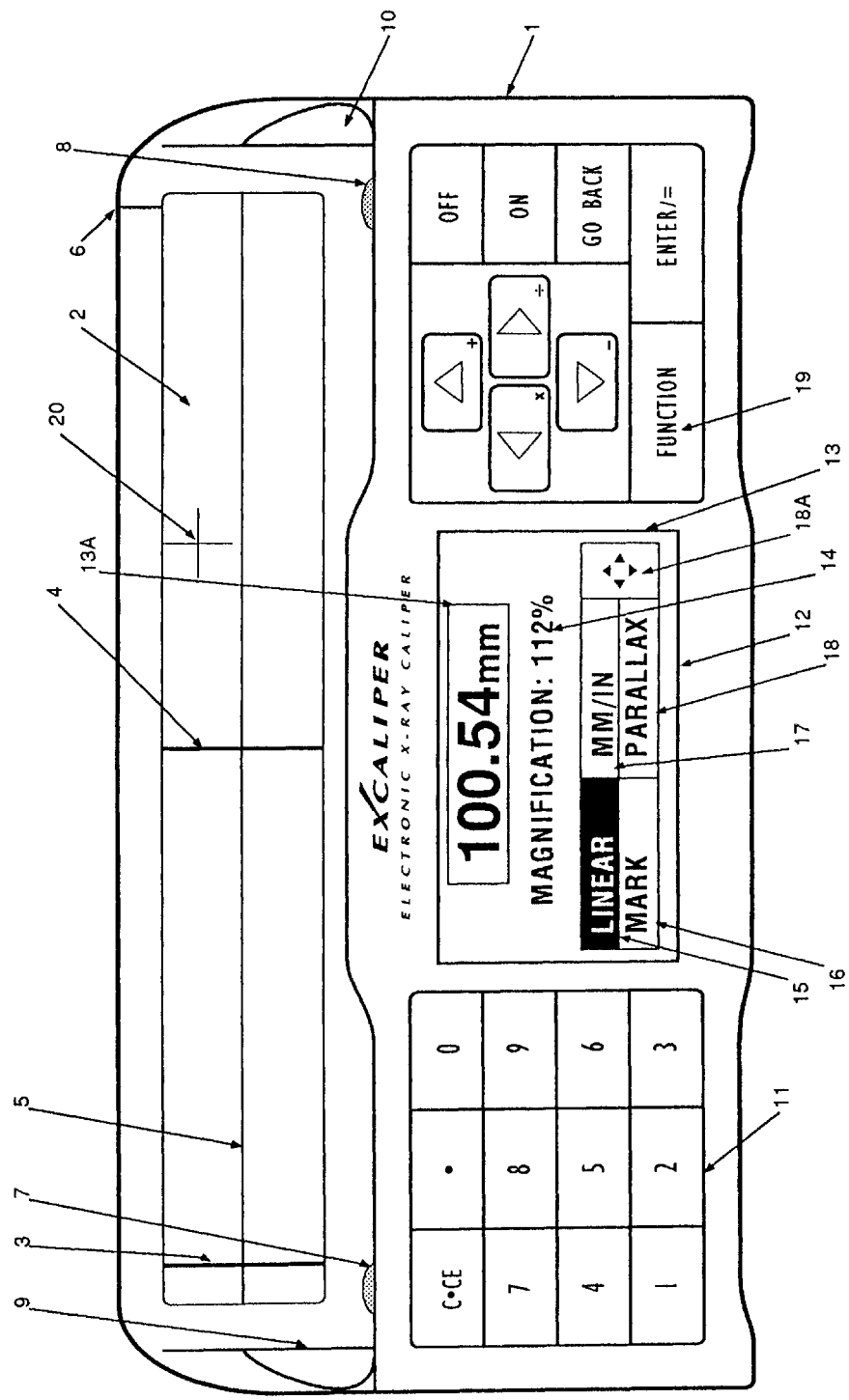
FIG. 1 shows view of the front of the device.

FIG. 1 shows a front view of the device 1, a liquid crystal device 2 ("LCD") in the upper portion of the device 1 whose frame is constructed from standard injection molded plastic, a left hand cursor 3 (shown in an energized state), a right hand cursor 4 (shown in an energized state), a silkscreened or scribed line 5 on the back surface of the glass of LCD 2 which line 5 extends the length of LCD 2 and is placed in the middle of LCD 2, an embossed mark 6 on the frame of device 1 which mark 6 extends vertically from LCD 2 and is placed approximately 2 millimeters ("mm") to the left of the right edge of the viewing area of the LCD 2, a left hand control button 7 for the LCD, a right hand control button 8 for the LCD, a numerical key pad 11, a readout screen 12 on a liquid crystal device ("LCD") 13, a readout cell 13A, a Magnification percentage cell 14, a Linear option cell 15, a Mark option cell 16, a millimeter/inch option cell 17, a parallax option cell 18, a directional keys symbol 18a, a control panel 19 with directional keys and various function control buttons ("Off," "On," "Go Back," "Function," and "Enter/="), and a cross-hair 20.

As is discussed below (for example in connection with FIG. 9), the LCD 13 at times displays a readout screen shown as 12 in FIG. 1 and at other times displays a prompt screen (see FIG. 9 for an example of a prompt screen under the heading "GLOSSARY & KEY TO SYMBOLS").

In FIG. 1, the device 1 is constructed with dimensions suitable for the device to be held in a human hand. In the preferred embodiment, the length of the device 1 is approximately 177 millimeters ("mm"), the length of the visible screen area of LCD 2 is approximately 153 mm, and the width of the device 1 is approximately 91 mm. Different dimensions may be used without departing from the scope or the spirit of the invention. In the preferred embodiment of FIG. 1, LCD 2 has only vertical annunciators and LCD 13 has pixels. LCD 13 is a standard graphic LCD. Both LCD 2 and LCD 13 are transparent. A reflective or lighted backing behind LCD 13 makes the alphanumeric information displayed on LCD 13 easier to read. The material used for the frame of device 1 could be any suitable material which could be molded or machined.

LCD 2 could be replaced by a graphic LCD.

LCD 2 could also be replaced by a mechanical cursor or cursors. The mechanical cursor or cursors could be of a type which includes, but is not limited to, manually positioned sliding mechanical cursors. For example, a mechanical cursor could be operated by a thumb wheel coupled to a mechanical linkage, a potentiometer, or a shaft encoder.

Figure 2:
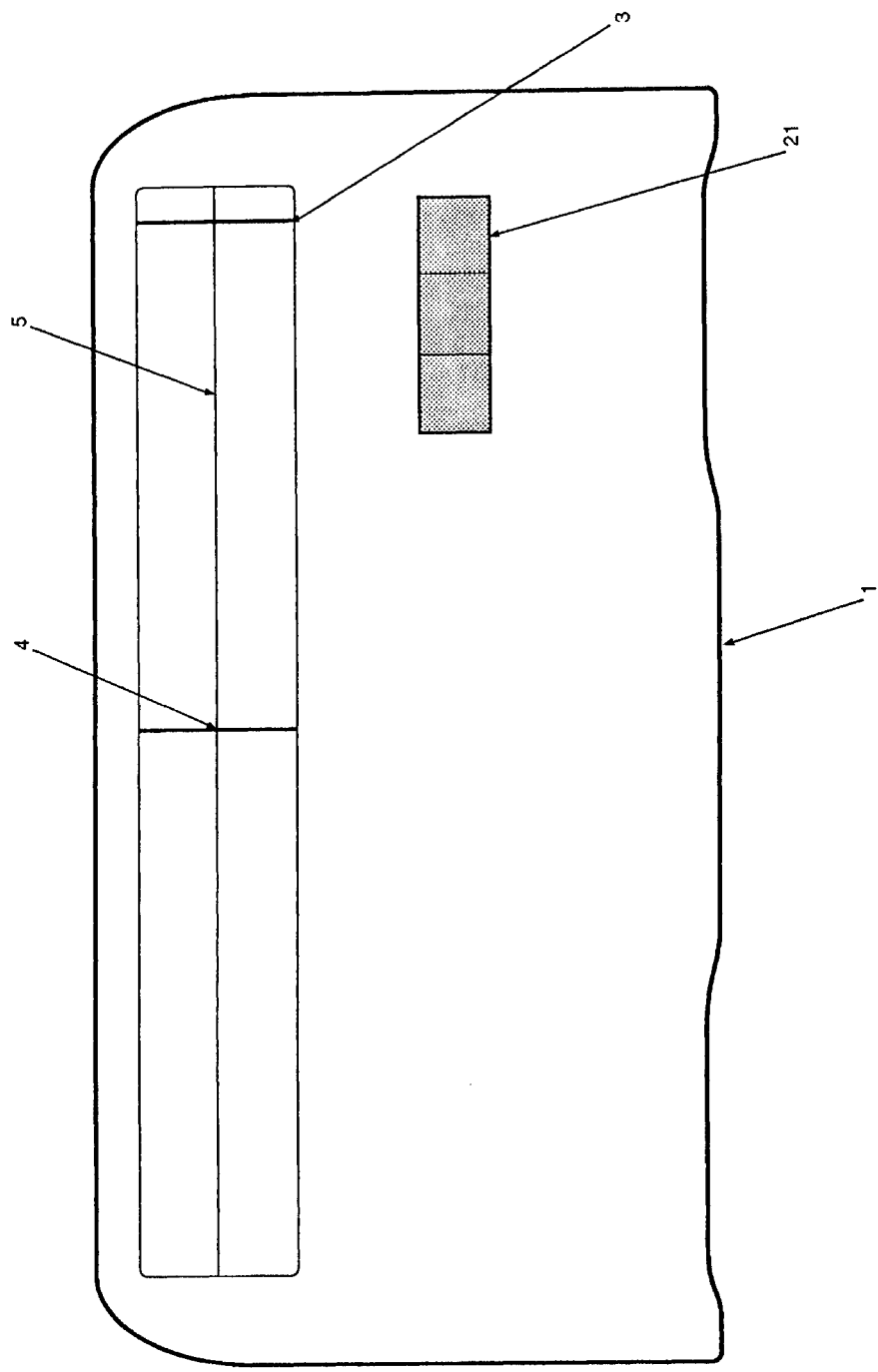
FIG. 2 shows a view of the back of the device.

FIG. 2 shows a view of the back of the device 1, a solar cell 21 for charging batteries (not shown in the figures) while the device is used on a lightbox such as that used for displaying radiographs, the silkscreened line 5, left hand cursor 3, and right hand cursor 4. The device could be manufactured with low profile rubber pads at the corners of the back of the device 1 which would provide some protection against mechanical shock to the device 1 and also provide some friction to stabilize the device when it is placed on a surface.

Figure 3:
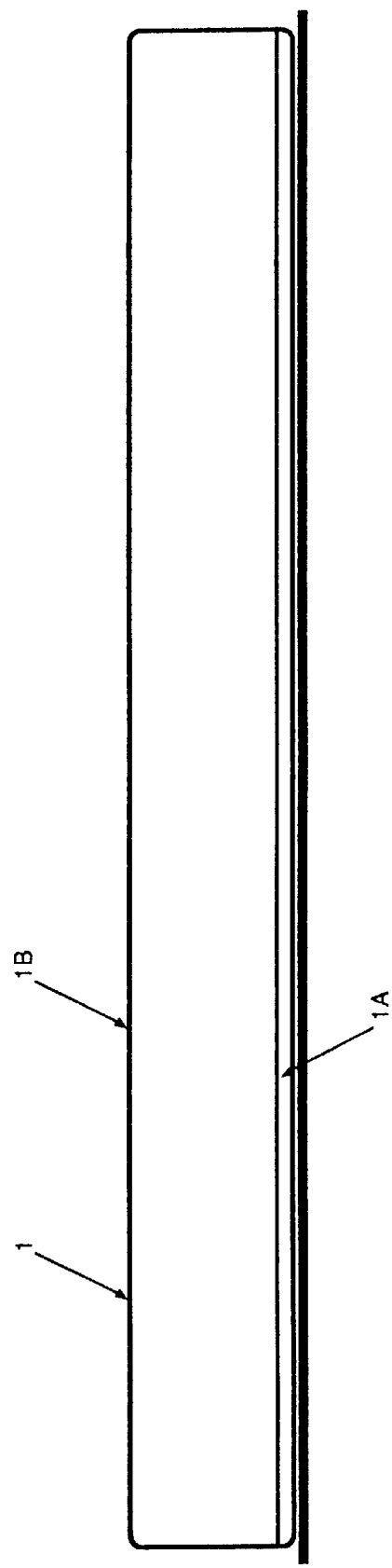
FIG. 3 shows a view of the bottom of the device.

FIG. 3 shows a view of the upper portion of the side of device 1, a lower portion 1a of the shell of device 1 and an upper portion 1b of the shell of device 1. The lower portion 1a and the upper portion 1b may be held together by fasteners or the lower and upper portions may be manufactured from plastic with snap-fit connectors.

Figure 4:
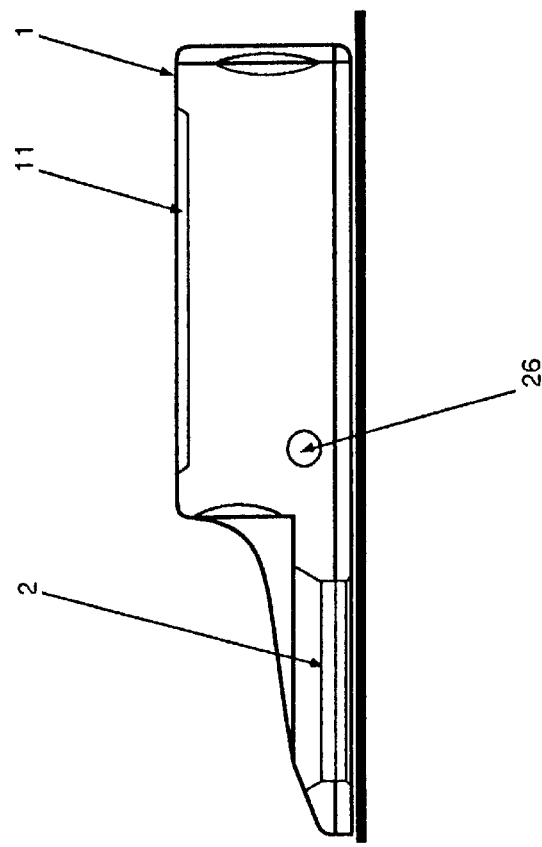
FIG. 4 shows a view of the side of the device.

FIG. 4 shows a side view of the left side of device 1. On the left of FIG. 4 is the area of the LCD 2. On the right of FIG. 4 is the area of the numerical key pad 11, and an input/output port 26. The input/output port 26 may provide for either a hard-wired connection from device 1 to an external computer or a wireless communication path using infrared or some other form of electromagnetic radiation or some other form of communication, including, but not limited to, ultrasound.

Figure 5:
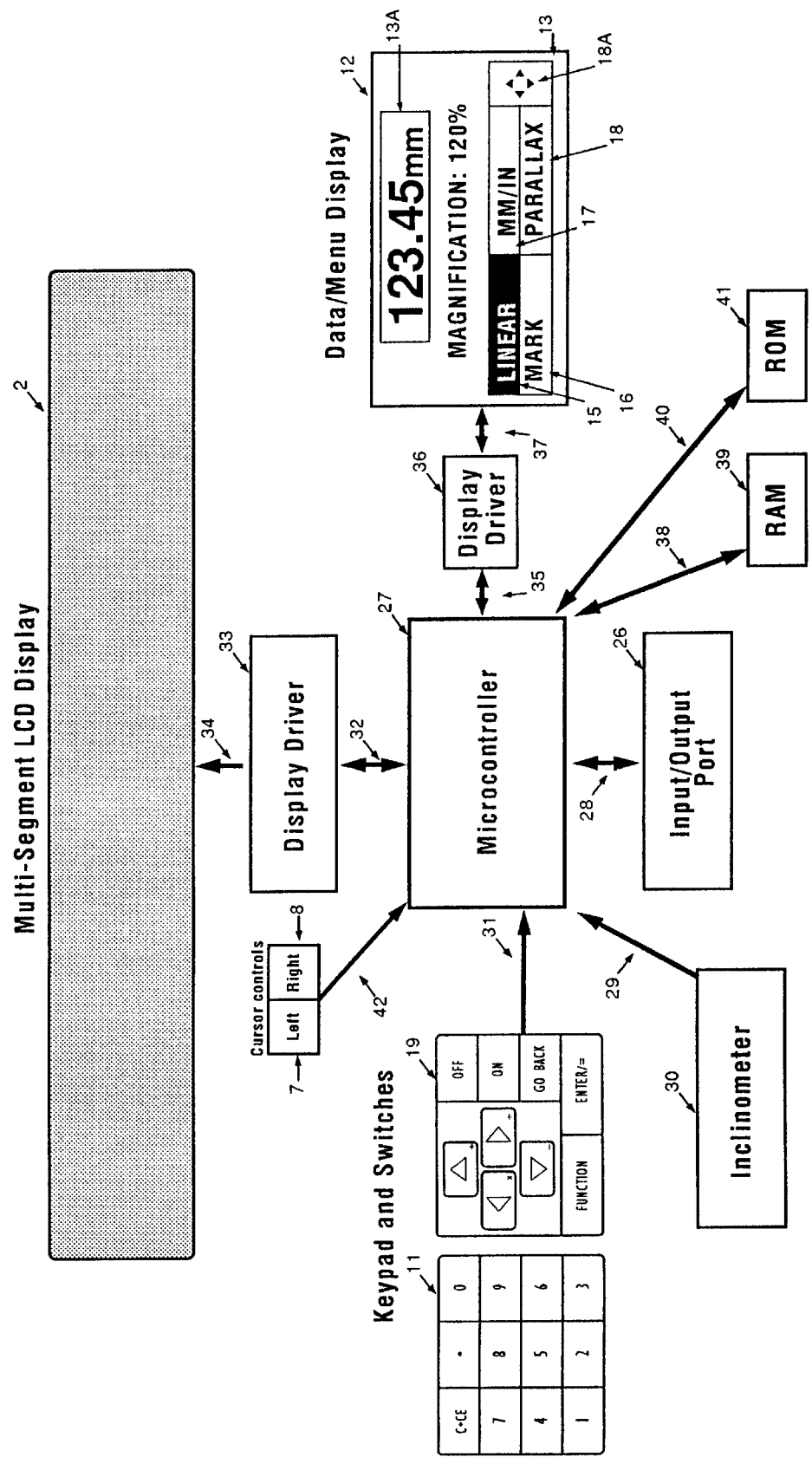
FIG. 5 shows a schematic block diagram of the electrical components of the device.

FIG. 5 shows a block diagram of the electrical components of the device.

FIG. 5 shows a microcontroller 27 connected to the input/output port 26 by a link 28, a link 29 connecting microcontroller 27 to an inclinometer 30, a link 31 connecting microcontroller 27 to numeric keypad 11 and control panel 19, a link 32 connecting microcontroller 27 to a primary display driver 33, a link 34 connecting primary display driver 33 to LCD screen 2, a link 35 connecting microcontroller 27 to a secondary display driver 36, a link 37 connecting secondary display driver 36 to LCD 13. Microcontroller 27 is also connected to one or more batteries which are inside device 1 and are not shown in the figures. Microcontroller 27 is also connected to solar cell 21 of FIG. 2 which solar cell is not shown in FIG. 5. Microcontroller 27 is also connected to left hand cursor control button 7 and right hand cursor control button 8 by link 42. Microcontroller 27 is also connected by link 38 to random access memory 39. Microcontroller 27 is also connected by link 40 to read only memory 41 which may be a ROM, EPROM, EEPROM, or other suitable device.

The primary LCD screen 2 used in the preferred embodiment of device 1 is a fixed segment type LCD which may be, inter alia, of the type manufactured by DCI, Inc., of Olathe, Kansas. However, any suitable LCD may be used as the primary LCD 2 of the device. The secondary LCD screen 13 used in the preferred embodiment of device 1 is a standard graphic type LCD which is generally available. The LCD used for LCD 13 may be, inter alia, of the type manufactured by Hitachi America, Inc. However, any suitable LCD may be used as secondary LCD 13 of the device. The microcontroller used in the preferred embodiment of device 1 may be a microcontroller manufactured by Motorola, Inc., Schaumburg, Ill., bearing Motorola part number 68HC11. However, any suitable microprocessor may be used. The computer language used to program the microprocessor in the preferred embodiment of device 1 is C. A suitable commercially available compiler is used to compile the source code written in C. However, any suitable computer language and compiler may be used if the computer language and compiler are compatible with and will operate in conjunction with the microprocessor selected for the device.

The inclinometer 30 used in the preferred embodiment of the device 1 should be one or more DC sensitive accelerometers of the type manufactured, for example, by Lucas Novasensor, Fremont, Calif., or Analog Devices, Inc., Woburn, Mass. However, any suitable angle sensor may be used. It is important that the outputs of the inclinometer can be coupled to or read into the microcontroller. It is also important that the devices controlling the cursors 3 and 4 and crosshair 20 be properly linked to the microcontroller. As an alternative to the accelerometer, a fluidic inclinometer may be used. For example, the inclinometer may be a T2 type inclinometer sold by U.S. Digital Corp., 17401 N.E. Stoney Meadows Drive, Vancouver, Wash. 98682-5614. If the device is used to measure angles in excess of 180 degrees, two accelerometers may be used with one accelerometer placed at right angles to the other accelerometer. Alternatively, one accelerometer could be used in conjunction with an orientation determining switch such as a mercury switch.

The primary display driver 33 in the preferred embodiment of the device 1 will have one or more integrated circuits in the display module. The primary display driver 33 and the secondary display driver 36 may be of any suitable commercially available type or may be custom made.

Figure 6:
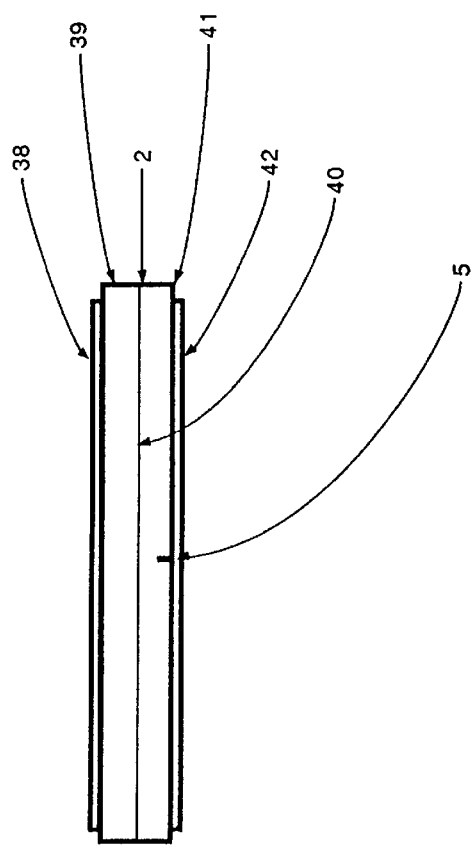
FIG. 6 shows a cross-sectional view of the LCD 2.

FIG. 6 shows a cross-sectional view of LCD screen 2 with top polarized film 38, top glass layer 39, annunciator 40, lower glass layer 41, lower polarized film 42, and the end of line 5 which is scribed into the bottom of lower glass layer 41.

Figure 7:
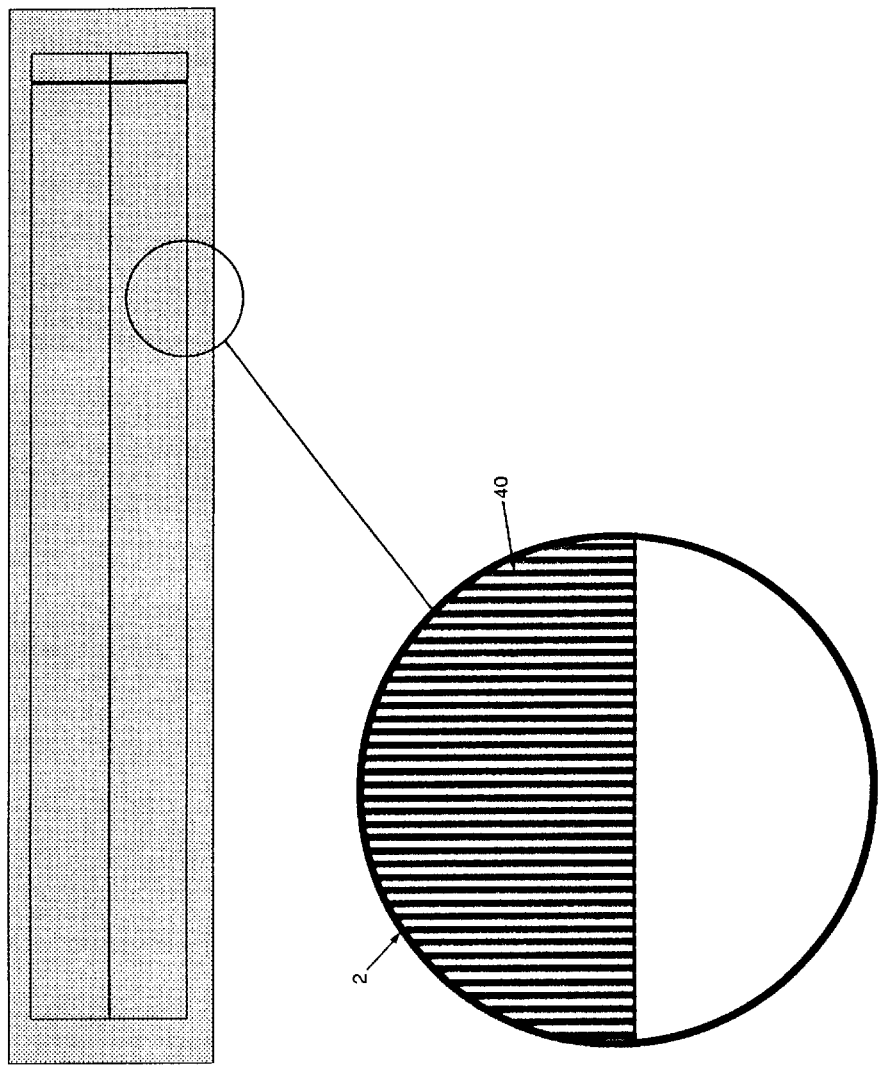
FIG. 7 shows a cross-sectional view of the LCD 2 showing annunciators being used in LCD 2.

FIG. 7 is a front view of an enlarged portion of LCD 2 showing a vertical annunciator 40.

Figure 8:
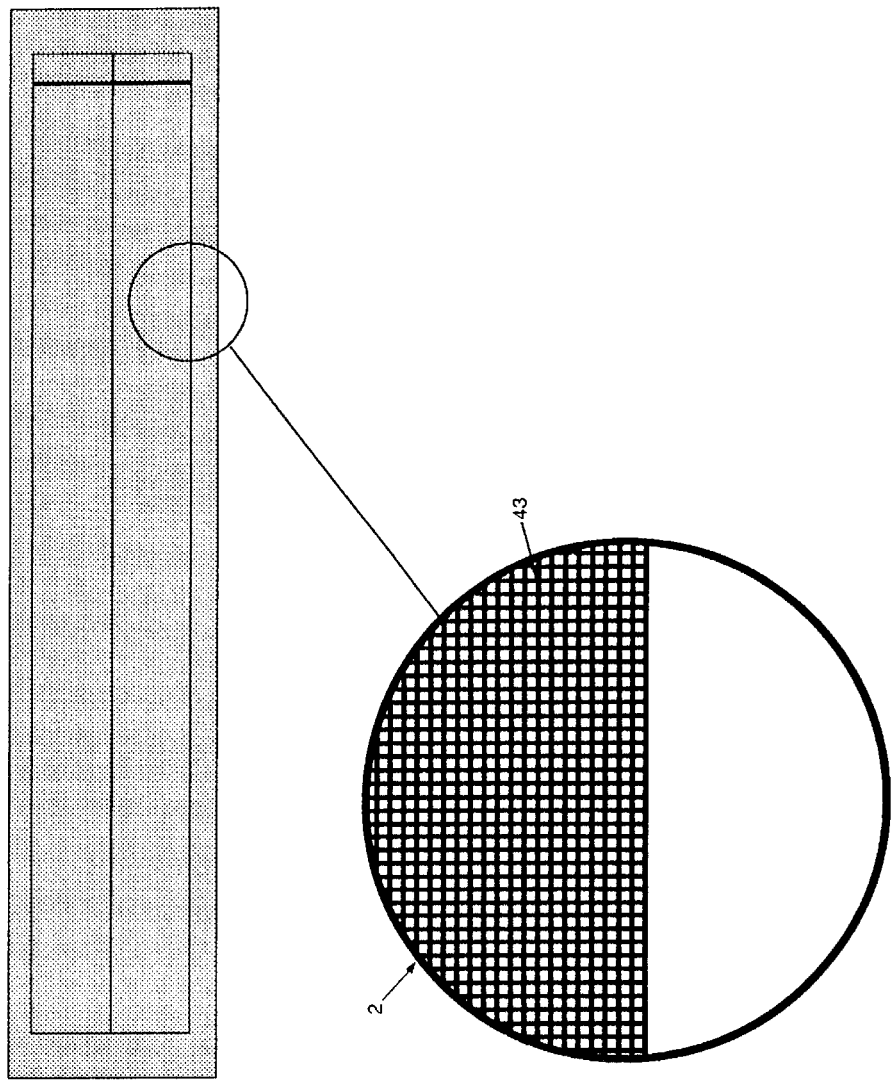
FIG. 8 shows the same cross-sectional view of the LCD 2 as in FIG. 7 but showing pixels being used in LCD 2.

FIG. 8 is a front view of an enlarged portion of LCD 2 showing pixels 43 in LCD 2 which pixels may be used in an alternative embodiment of the device 1. Pixels are also used in graphic LCD 13 shown, for example, in FIGS. 1 and 5.

FIG. 9 explains the nomenclature used in FIGS. 10A, 10B, 11A, 11B, 11C, 11E, 11F, 12, and 13 which are flow charts explaining aspects of the operation of the device. The boxes in the upper left of each block indicate a button which is pressed by the user of the device or an action taken by the user of the device. The number in the lower left of each block is a box identification number. The description at the top of each box describes the visual feedback from the device or the function being performed by the device. The information which would appear on the LCD screen 13 after pressing the button(s) or taking the action stated on the left side of each sub-flow chart is shown in the box on the right of each block. The LCD 13 can either display a readout screen as shown in FIG. 9 or a prompt screen as shown in FIG. 9. When the LCD 13 displays a readout screen:

1. the readout cell 13*a* at the top of the LCD 13 screen contains information which is selectable and editable;

2. the magnification percentage cell 14 contains information which is selectable and editable (the number in the magnification cell 14 changes as the magnification of the radiograph or scan being analyzed changes);

3. the linear option cell 15, mark option cell 16, millimeter/inch option cell 17, and parallax option cell 18 are selectable but the data in these cells is not editable;

4. the directional keys symbol 18*a* is not selectable or editable.

A blinking highlight (reversing out or switching the normal appearance of black alphanumeric characters on a white background for white alphanumeric characters on a black background (which functions in the same way as cursors in some text editing programs used with personal computers)) only appears in the editable data cells (i.e., the readout cell 13*a*, the magnification cell 14, the name data which may appear on LCD 13 during the set up mode of the device, and the telephone number which also may appear on LCD 13 during the set up mode of the device. When the user types or enters an alphanumeric character, the character appears on the screen and the highlight (or, in some text editing programs used with personal computers, a cursor) moves to the next space or alphanumeric character. A prompt tells the user to perform a specific function. The cursors are two vertical lines 3 and 4 on the transparent LCD screen 2. The default position for the left cursor is 5 mm from the left edge of LCD screen 2. The default position for the right cursor is centered on LCD screen 2. The control button symbol is shown at the bottom of FIG. 9. The two control buttons 7 and 8 are used to move the cursors in certain modes of the device. The two control buttons are also used in the ANGLE mode (explained below in conjunction with FIG. 12) to set angle origins and display angle data.

SET UP MODE

Figure 10A:
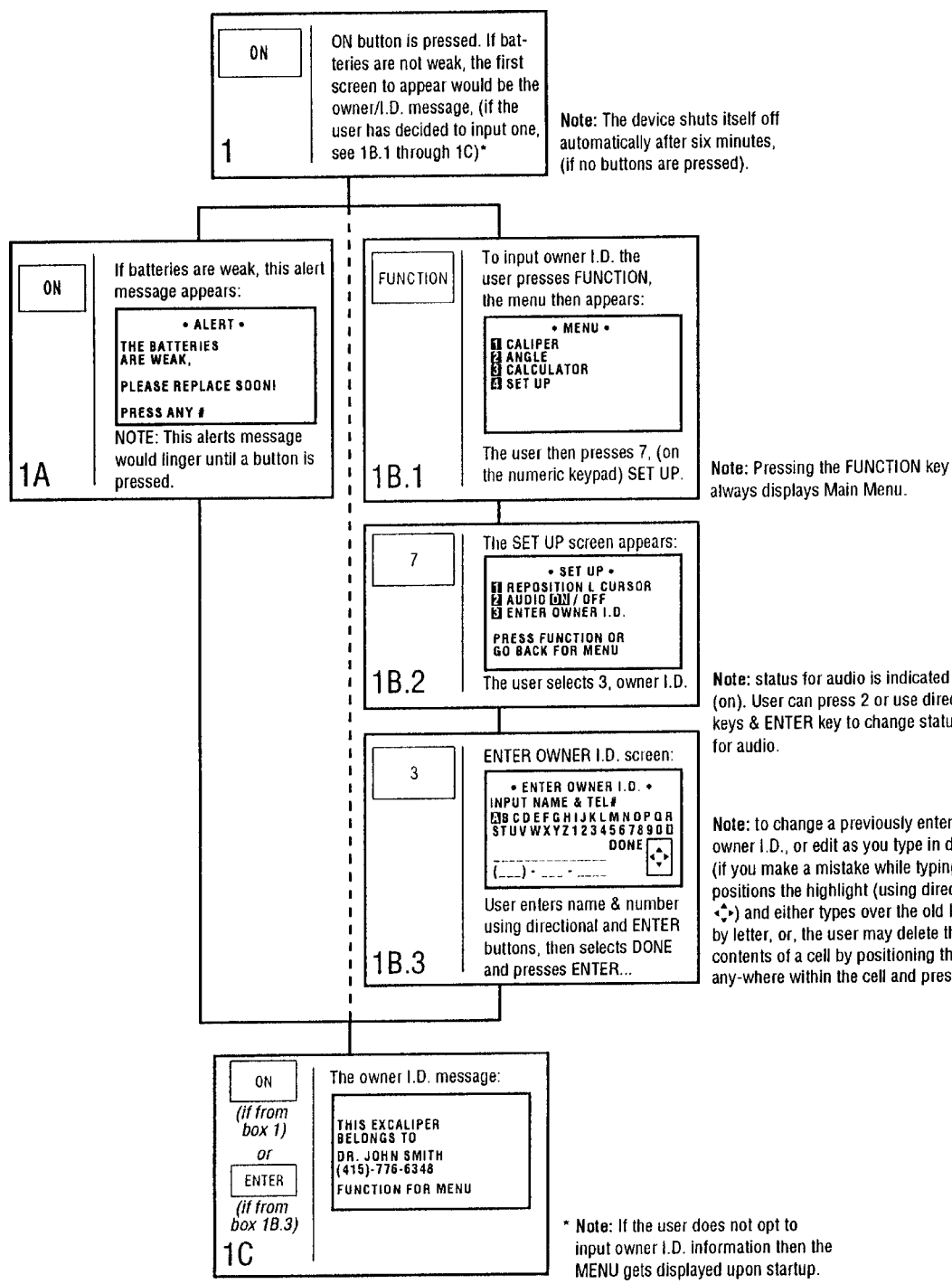
FIG. 10A shows the first of two flow charts explaining the operation of the Set Up Mode of the device.

FIG. 10A (consisting of sub-flow charts 1, 1A, 1B.1, 1B.2., 1B.3, and 1C) is a series of flow charts which explain a portion of the operation of the Set Up mode of the device. FIG. 10A shows that the if the batteries are weak (i.e., the measured potential is less than some pre-determined percentage of the maximum charge), the user sees a screen warning about low batteries,, a screen with information about the owner of the device (if such information has been entered into the device previously), and then a screen with the main menu of the device. FIG. 10A shows that the if the batteries are not weak, the user sees a screen with information about the owner of the device (if such information has been entered into the device previously), and then a screen with the main menu of the device.

Sub-flow chart 1A shows that the following message appears on LCD screen 13 if the batteries are weak: "ALERT THE BATTERIES ARE WEAK, PLEASE REPLACE SOON! PRESS ANY #". The immediately preceding alert message stays on the LCD screen 2 until any button is pressed on numeric keypad 11. If information about the owner of the device has previously been entered, after any button on the numeric keypad 11 is pressed, the device then displays the information shown in sub-flow chart 1C. The user presses the FUNCTION key on control panel 19 to shift from sub-flow chart 1C to sub-flow chart 1B.1 (the main MENU).

Sub-flow chart 1 of FIG. 10A shows that if the batteries are not weak then after the "ON" button of control panel 19 is pressed an owner/identification message (as shown in sub-flow chart 1C) appears on LCD screen 13 if the user has previously provided owner identification information. If the user has not provided owner identification information then the main MENU sub-flow chart 1B.1 will appear when the ON button of the device is pressed. (The owner/identification message is explained below with reference to sub-flow charts 1B.1, 1B.2, 1B.3, and 1C of FIG. 10A. The Main Menu is discussed below with reference to FIG. 10A, sub-flow chart 1B.1.) The device will shut itself off automatically if no button is pressed for six minutes.

Sub-flow chart 1B.1 of FIG. 10A shows that when the user of the device presses the FUNCTION key of control panel 19 the following Main Menu appears on the LCD screen 13 under the heading "MENU":
1 CALIPER
2 ANGLE
3 CALCULATOR
4 SET UP.

To select the CALIPER mode, the user presses the "1" key on numeric keypad 11 (the operation of the CALIPER mode is explained below with reference to FIGS. 11A-11F).

To select the ANGLE mode, the user presses the "2" key on numeric keypad 11 (the operation of the ANGLE mode is explained below with reference to FIG. 12).

To select the CALCULATOR mode, the user presses the "3" key on numeric keypad 11 (the operation of the CALCULATOR mode is explained below with reference to FIG. 13).

To select the SET UP function, the user then presses the "14", key on the numeric keypad 11 (pressing the FUNCTION key of the control panel 19 always displays the Main Menu on the LCD screen 2).

Sub-flow chart 1B.2 of FIG. 10A shows that when the user selects the SET UP screen, the following appears on LCD screen 13 under the heading "SET UP":
1 REPOSITION L CURSOR
2 AUDIO ON/OFF
3 ENTER OWNER I.D.
PRESS FUNCTION OR GO BACK FOR MENU The GO BACK key will return the LCD screen 13 to the immediately prior screen. This process continues if the user continues to press the GO BACK key until the most recent appearance of the MAIN menu is reached.

The function of repositioning the left cursor (accessed by pressing the "1" button on numeric keypad 11 of device 1 when the "SET UP" screen appears) is explained below with reference to subflow charts 2A.1, 2A.2, 2A.3, 2A.4, 2B.1, 2B.2, 2B.3, and 2B.4 of FIG. 10B.

The audio selection ("ON" or "OFF") may only be changed when device 1 displays the SET UP screen of sub-flow chart 1B.2 on LCD 13. Initially, device 1 is set with the AUDIO in the ON state. When the "Audio" is "ON," the device emits a beep as each key or control is touched. When the "Audio" is "OFF," the device does not emit a beep as each key or control is touched. The function of changing the audio selection from "ON" to "OFF" (which switching function is accessed by pressing the "2" button on numeric keypad 11 of device 1 when the "SET UP" screen appears (as shown in sub-flow chart 1B.2)) is accomplished by using the left and right arrow keys of control panel 19. If the Audio is in the "ON" state, the user switches to the "OFF" state by pressing the right arrow directional key and then "ENTER" on control panel 19. If the Audio is in the "OFF" state, the user switches to the "ON" state by pressing the left arrow directional key and then "ENTER" on control panel 19.

To display the owner identification input screen (as shown in sub-flow chart 1B.3) on LCD screen 13, the user presses the "3" key on numeric keypad 11 when the SET UP screen of sub-flow chart 1B.2 appears on LCD 13. The owner identification input screen (of subflow chart 1B.3) may only be entered immediately after device 1 displays the SET UP screen of sub-flow chart 1B.2 on LCD 13.

Sub-flow chart 1B.3 of FIG. 10A, shows that the owner identification screen consists of the following message:
ENTER OWNER I.D.
INPUT NAME & TEL#
ABCDEFGHIJKILMNOPQR STUVWXYZ1234567890
(an empty rectangle indicating a space) (a period) DONE
(a symbol representing the directional keys) - - - - - - - -
- - - - - - - - - -( _ _ )- _ _ - _ _ _ _

Each letter of the user's name and each number of the user's telephone number is selected by using the directional keys of the control panel 19 to position the blinking highlight over the letter or number to be selected and then pressing the "ENTER" button on the control panel 19. The maximum length of the user's name is 20 characters. As each alphanumeric character is selected, device 1 places the selected character in the next available position on the owner identification input screen. If a letter is selected after the line for the user's name has been completed, the letter will not be entered in the telephone number. Only numbers will be entered by device 1 on the telephone number line of the owner identification input screen. When the entire name and telephone number have been selected (character by character) and appear on LCD screen 13, the user selects "DONE" (by placing the highlight over "DONE" on the owner identification screen) and presses "ENTER" to complete entry of the name and telephone number in the memory of device 1. The user may delete an entire name or telephone number by positioning the highlight on any alphanumeric character in the previously selected name or telephone number and pressing the "C/CE" button of numeric keypad 11 to remove one character at a time. After a character has been selected for each of the available spaces in the owner identification screen, device 1 displays the owner identification message as shown in sub-flow chart 1C. The user then presses the "FUNCTION" key of control panel 19 to return to the MAIN menu (shown in sub-flow chart 1B.1).

If owner identification information (e.g., Dr. John Smith, (415) 776-6348) has been stored in the device, then the following owner identification message screen appears on LCD 13 when the "ON" button is pressed to start the device:
THIS EXCALIPER
BELONGS TO
DR. JOHN SMITH
(415)-776-6348
FUNCTION FOR MENU The user continues by pressing the "FUNCTION" key of control panel 19 to cause the main MENU (shown in sub-flow chart 1B.1) to appear on LCD screen 13.

If the user does not input any owner identification information and the batteries are not weak, then the function MENU of sub-flow chart 1B.1 is the first screen of information to appear on LCD screen 13 after the device 1 is activated. As discussed above, if the batteries are weak, a message about the battery state (as shown in sub-flow chart 1A) will appear before the owner identification message (shown in sub-flow chart 1C).

Figure 10B:
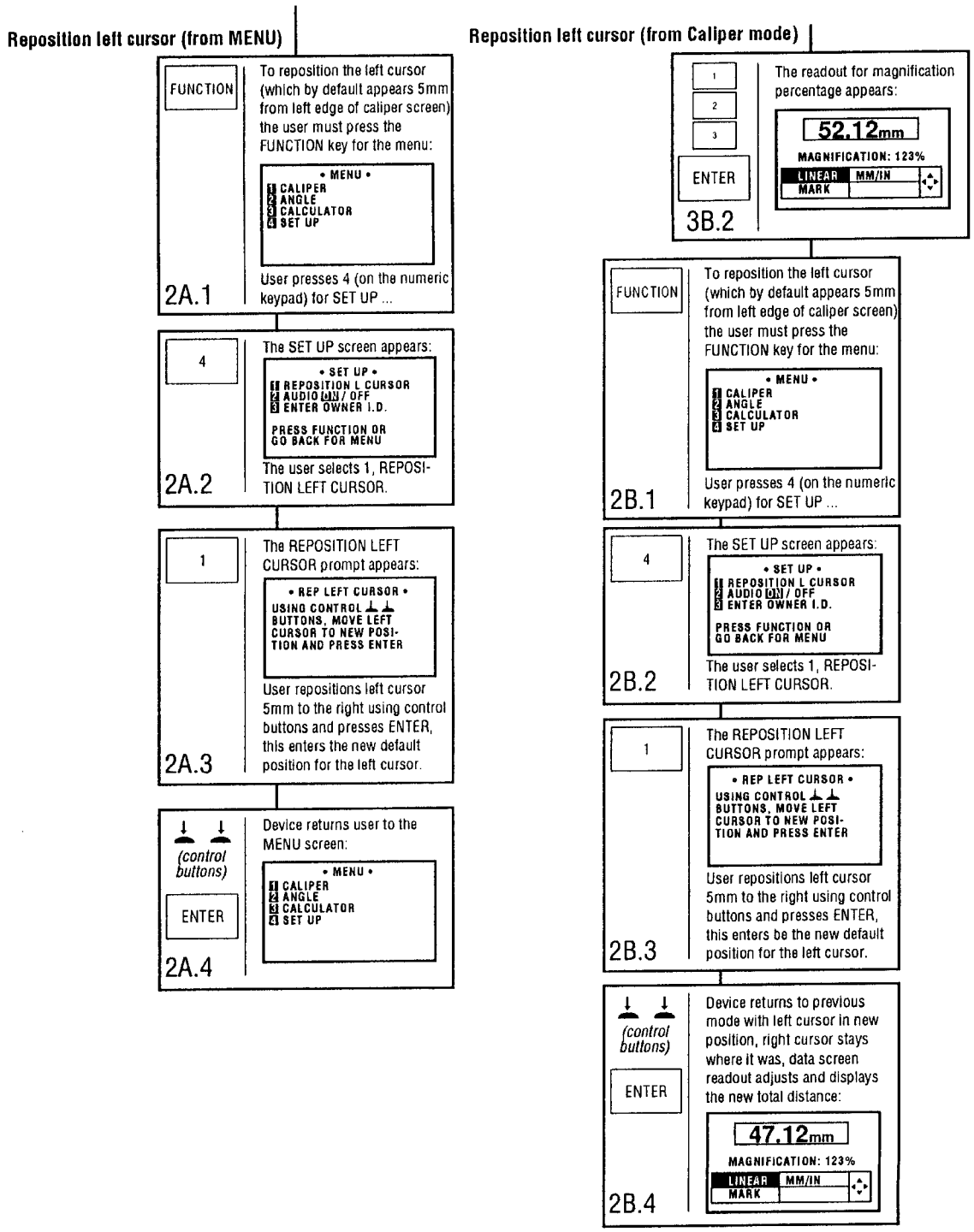
FIG. 10B shows the second of two flow charts explaining the operation of the Set Up Mode of the device.

FIG. 10B (consisting of sub-flow charts 2A.1, 2A.2, 2A.3, 2A.4, 2B.1, 2B.2, 2B.3, 2B.4, and, for continuity, 3B.2) shows the second of two flow charts explaining the operation of the Set Up mode of the device. The function of repositioning the left cursor is accomplished in the SET UP mode as discussed below with respect to FIG. 10B.

Sub-flow chart 2A.1 shows that depressing the "4" key on the numeric keypad 11 selects the SET UP menu as shown in sub-flow chart 2A.2.

Sub-flow chart 2A.2 shows that depressing the "1" key on the numeric keypad 11 selects the prompt for "REPOSITION L CURSOR" (reposition left cursor) as shown in sub-flow chart 2A.3

Sub-flow chart 2A.3 shows that the user uses the left hand cursor control button 7 and right hand cursor control button 8 to reposition the left cursor 3 to its new default position a distance of, for example, 5 mm to the right on the LCD 2. The user then presses the "ENTER" button which enters the new default position for the left cursor 3. After pressing the "ENTER" button, the device 1 returns the user to the MAIN menu screen as shown for example, in sub-flow chart 2A.4. The initial default position for the left cursor 3 is 5 millimeters ("mm") to the right of the left edge of LCD screen 2. The beginning default position for the left cursor may be anywhere between the width of three pixels or three annunciators to the right of the left edge of LCD screen 2 and the width of three pixels or three annunciators to the left of the vertical centerline of LCD screen 2. In the SET UP mode, only the left cursor is active. In the SET UP mode, pressing the left hand cursor control button 7 moves the left cursor 3 to the left. In the SET UP mode, pressing the right hand cursor control button 8 moves the left cursor 3 to the right. The initial default position for the right cursor 4 is the vertical centerline of LCD screen 2. In all modes other than the SET UP mode, only the right cursor 4 is active. When the right cursor is active, pressing the left hand cursor control button 7 moves the right cursor 4 to the left and pressing the right hand cursor control button 8 moves the right cursor 4 to the right.

The effect of moving the left cursor 3 a distance of 5 mm to the right while the right cursor 4 stays in a constant position is to reduce the inter-cursor spacing. The effect of changing the inter-cursor spacing may be seen in, for example, the CALIPER mode of device 1 which is shown beginning in the immediately following paragraph below with respect to FIGS. 11A–11F. If, as shown in FIG. 10B on sub-flow chart 3B.2, the inter-cursor spacing is 52.12 mm, then selecting the SET-UP mode (sub-flow chart 2B.1), selecting the REPOSITION LEFT CURSOR option (sub-flow chart 2B.2), and repositioning the left cursor 5 mm to the right (sub-flow chart 2B.3) while maintaining the position of the right cursor 4 will result in a new spacing of 47.12 mm as shown on LCD 13.

CALIPER MODE

Figure 11A:
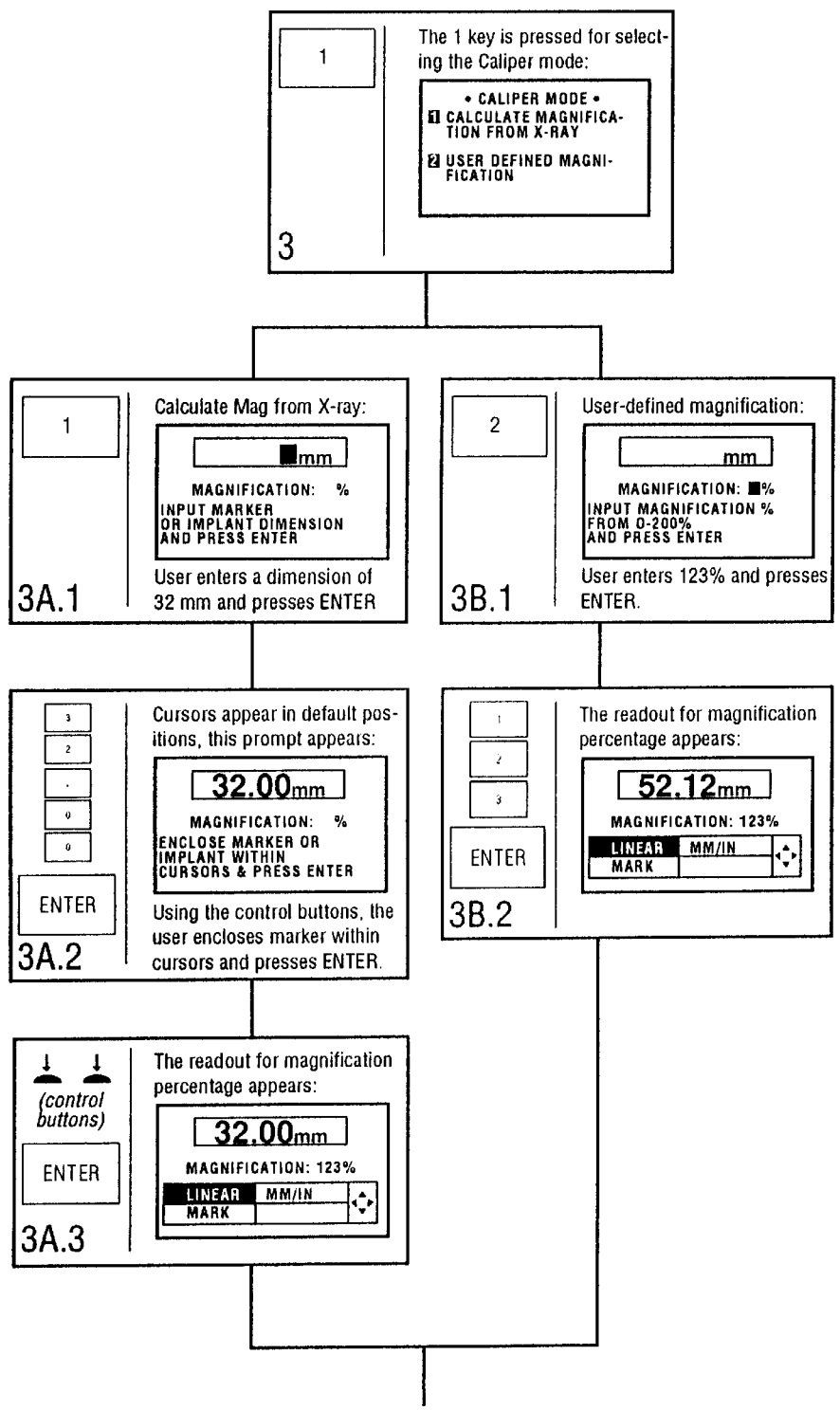
FIG. 11A shows the first of five flow charts explaining the operation of the Caliper Mode of the device.

FIG. 11A (consisting of sub-flow charts 3, 3A.1, 3A.2, 3A.3, 3B.1, and 3B.2) shows the first of five flow charts explaining the operation of the Caliper mode of the device. As mentioned above (FIG. 10A, sub-flow chart 1B.1), to select the CALIPER function, the user presses the "1" key on numeric keypad 11 when the device 1 displays the main MENU. If the batteries are not weak and the user identification information has not been entered, the main MENU will display automatically when the device 1 is switched on by pushing the "ON" button. If the batteries are not weak and the user identification information has been entered, the user identification information will display automatically when the device 1 is switched on by pushing the "ON" button.

Sub-flow chart 3 shows that in the Caliper mode, two basic options are available. These options are Calculate Magnification From X-ray (selected by pressing number "1" on the numeric keypad 11) and User Defined Magnification (selected by pressing number "2" on the numeric keypad 11).

Sub-flow chart 3A.1 shows that in the Calculate Magnification From X-ray mode, the user enters the known dimension of a radio-opaque marker or an implanted device appearing in a radiograph or scan. An example of 32 mm is shown in the readout cell 13a. In this case, 32 mm is the width of the marker being used and this width is entered by pressing the keys on the numeric keypad 11 for "32.00" and then pressing the Enter key on the control panel 19.

Sub-flow chart 3A.2 shows that the user must then:

1. place the device 1 on the radiograph or scan (it is understood that the back of the device should be in contact with the radiograph or scan and the plane of the back of the device should be essentially parallel to the plane of the radiograph or scan in a manner which allows the user to look through LCD 2 and view the radiograph or scan);

2. place the left cursor 3 on the leftmost edge of the marker on the radiograph or scan which marker is observed by looking through the transparent LCD 2 to the;

3. place the right cursor 4 on the rightmost edge of the marker on the film; and 4. press the ENTER button on control panel 11.

Sub-flow chart 3A.3 shows a magnification percentage of 123% in the Magnification cell 14 which percentage has been calculated by the software and microprocessor 27 in device 1 using the inputs of the known size of the marker (32 mm) and the positions of the cursors 3 and 4. This means that the measurements of the objects whose images appear on the radiograph must be divided by 123% to determine the objects' actual measurements. In all cases (including the case of scans which may have an image size less than actual size), the image size is divided by the magnification percentage to determine the actual object size. The user can then use device 1 to measure other features of interest on the radiograph. Once the cursors are placed at the opposing ends of the distance to be measured, the device 1 (knowing the appropriate magnification percentage for the radiograph) can provide a readout in readout cell 13a on LCD 13 of the actual distance being measured.

If LCD screen 2 is comprised of annunciators, each cursor is three (3) annunciators wide. For calculation purposes, the position of the left cursor 3 is the rightmost annunciator of the three annunciators which form the cursor. For calculation purposes, the position of the right cursor 4 is the leftmost annunciator of the three annunciators which form the cursor. If LCD screen 2 is comprised of pixels, each cursor is three (3) pixels wide. For calculation purposes, the position of the left cursor 3 is the rightmost column of pixels of the three columns of pixels which form the cursor. For calculation purposes, the position of the right cursor 4 is the leftmost column of pixels of the three columns of pixels which form the cursor.

Sub-flow chart 3A.3 also shows that the highlight is on the Linear option cell 15 which means that the device 1 is ready to measure a distance longer than the device 1.

Sub-flow chart 3B.1 shows that the device allows for a User-defined Magnification which is selected by pressing "2" on numeric keypad 11 after device 1 enters the CALIPER mode (as shown in sub-flow chart 3). After selecting User-defined Magnification, the user can enter a user-defined magnification percentage (the example shown is for 123%) by pressing "123" on numeric keypad 11 and the "ENTER" key on control panel 19.

Sub-flow chart 3B.2 shows the user selected magnification percentage of 123% appears in the Magnification percentage cell 14. Sub-flow chart 3B.2 also shows that the device 1 has divided the distance between the cursors by 123% to determine the actual distance (shown in the example as 52.12 mm) represented by the current inter-cursor spacing.

At least one of the readout cell 13a and the Magnification percentage cell 14 must have a value at all times. Thus, the user must first clear and input a new value into one of the cells 13a or 14 and then do the same for the other cell 14 or 13a.

Whether the user selects "Calculate Magnification From X-Ray" or "User Defined Magnification," LCD screen 13 will return to the screen shown in sub-flow chart 3B.2 or 3A.3 (which is the same screen as the screen shown in sub-flow chart 3B.2 but with different values).

Figure 11B:
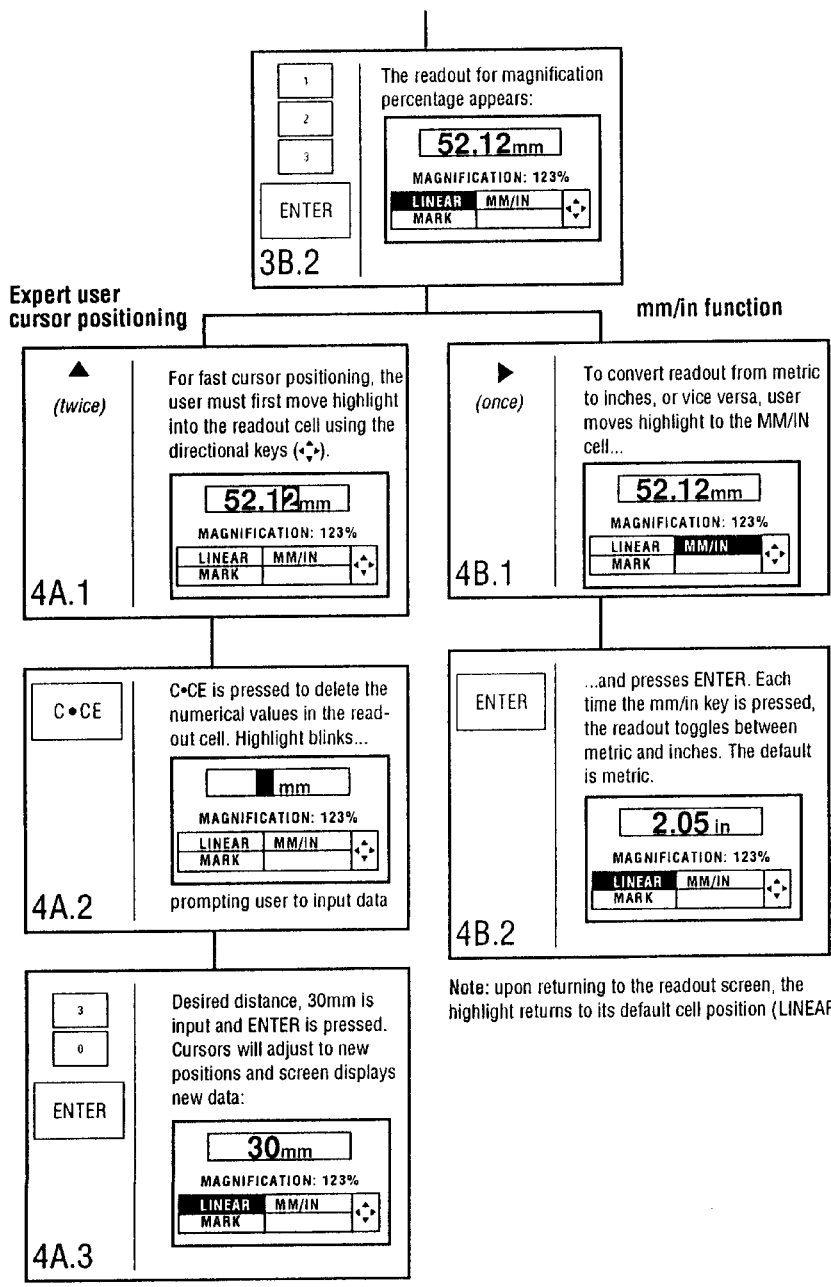
FIG. 11B shows the second of five flow charts explaining the operation of the Caliper Mode of the device.

FIG. 11B (consisting of sub-flow charts 4A.1, 4A.2, 4A.3, 4B.1, and 4B.2 plus a repeat for continuity of sub-flow chart 3B.2 from FIG. 11A) shows the second of five flow charts explaining the operation of the Caliper mode of the device.

Sub-flow chart 4A.1 shows a means for fast cursor positioning. The user first moves the highlight from the previous position in the Linear option cell 15 (as shown in sub-flow chart 3B.2) to a new position in readout cell 13a. The user moves the highlight by using the directional keys (in this case the "UP" directional key) on control panel 19. When the highlight is placed in readout cell 13a, the highlight appears over the rightmost digit. The user may move the highlight in readout cell 13a by using the right and left directional keys on control panel 19. Pressing the right directional key moves the highlight to the right and pressing the left directional key moves the highlight to the left. The user then presses the "C/CE" key on numeric keypad 11 which clears the entry in readout cell 13a. The user then enters the desired spacing of the cursors (that is, the user wants the inter-cursor spacing to reflect an actual distance (as opposed to a distance on a radiograph or scan)) which spacing in the example shown is 30 mm. The user enters (in the example shown) a new object size (or actual distance) of 30 mm by pressing "30.00" on numeric keypad 11 and "ENTER" on control panel 19. The number in the Magnification percentage cell 14 remains the same. When the number in the readout cell 13a of LCD 13 is changed, the right hand cursor moves to a position set by the new number in the readout cell 13a and the number in the Magnification percentage cell 14. To change the number in the readout cell 13a, the user must move the movable highlight (shown in sub-flow chart 4A.1 over the last digit in the readout cell 13a) to the digit the user wishes to change. The movable highlight is moved using the directional keys on the control panel 19.

After the movable highlight is placed in the cell the user wishes to change, sub-flow chart 4A.2 shows that to clear the number entered in the readout cell the user must press the Clear/Clear Entry ("C/CE") key on numeric keypad 11. If the "C/CE" button is pressed, the highlight will begin to blink to prompt the user to enter a new value in readout cell 13a. Alternatively, the user can place the movable highlight over the digit the user wishes to change and change the digit by pressing a new number on numeric keypad 11. After a new digit is entered, the highlight moves one digit to the right. The highlight will skip over the decimal point when the digit to the immediate left of the decimal point is changed.

Sub-flow chart 4A.3 shows that after entering a new number in the readout cell 13a the user must press the "Enter" key to complete the change of the number in the readout cell 13a. After the new number is entered, the right cursor will adjust its position to the new number and percentage magnification and the readout cell 13a and magnification percentage cell 14 will display the new information.

Sub-flow chart 4B.1 shows that the first step in converting the units in the readout cell 13a from millimeters to inches is to use the directional keys on control panel 19 to position the movable highlight over the Millimeter/Inches option cell 17.

Sub-flow chart 4B.2 shows that the second and last step in converting the units in the readout cell 13a from millimeters to inches is to press the "Enter" key in the control panel 19. When the movable highlight is positioned over the Millimeter/Inches option cell 17, each time the "Enter" key in the control panel 19 is pressed, the units in the readout cell 13a change (that is, pressing "Enter" changes the units in the readout cell 13a from millimeters to inches or from inches to millimeters). When the "ENTER" key is pressed, the highlight returns to the Linear option cell 15 and the new unit of measurement selected (millimeters or inches) appears in readout cell 13a. The default unit of measurement is millimeters.

At any time, the user can switch modes by pressing the Function key on the control panel 19 to return to the Main menu and then selecting a new function.

FIG. 11C (consisting of sub-flow charts 5A.1, 5A.2, 5A2.1, 5B.1, 5B.2, and, for continuity, 3B.2) shows the third of five flow charts explaining the operation of the Caliper Mode of the device.

Sub-flow chart 5A.1 explains how the user can begin to change the value in the magnification percentage cell 14. First, the user uses the directional keys on control panel 19 to move the highlight to magnification percentage cell 14. When the highlight is first placed on the magnification percentage cell, the highlight is on the rightmost digit. The highlight can then be moved within the cell by using the right and left directional keys on control panel 19. In the example shown, the highlight is placed on the middle digit in the magnification percentage cell 14. The user can change the number in the magnification percentage cell 14 by pressing the "C/CE" key and the keys for the new number on the numeric keypad 14 or by replacing the digits in magnification percentage cell 14 one at a time. In either case, after the new number is in the magnification percentage cell 14, the user must press "Enter" on control panel 19. In the example shown, the magnification percentage is changed from 123% to 116%.

Sub-flow chart 5A.2 shows that the readout cell 13a readjusts to account for the new magnification percentage. The cursors are the same distance apart in sub-flow chart 5A.1 and 5A.2.

Sub-flow chart 5A.2.1 shows that the user may press the "GO BACK" key on the control panel 19 to return to previous screens within the CALIPER mode until reaching the main MENU screen.

Figure 11D:
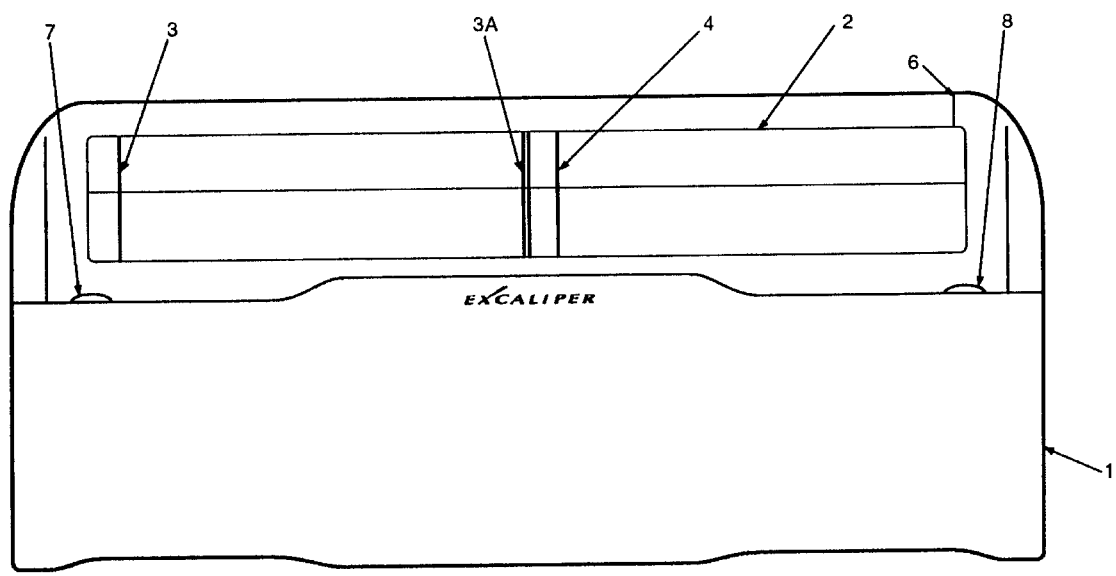
FIG. 11D shows a front view of the device after the MARK mode is selected.

Sub-flow chart 5B.1 shows that the user may select the MARK function by using the directional keys on the control panel 19 to move the highlight to the MARK cell 16 on the graphic LCD 13 and then pressing the "ENTER" button on control panel 19. When the MARK function is selected, a third or mark cursor 3A appears in the location previously occupied by the right cursor 4 and the right cursor moves 5 mm to the right of its original location just before the MARK function was selected (as shown in FIG. 11D). The readout cell 13A will then show the total distance from the left cursor 3 to the right cursor 4 and the mark distance from the left cursor 3 to the mark 3A. The mark distance is followed by a "5" to show the mark cursor to right hand cursor spacing of 5 mm.

Sub-flow chart 5B.2 shows that while using the MARK function in the Caliper mode the user may press the "C/CE" key on the numeric keypad 11 to end use of the MARK function and remove the mark cursor 3A from LCD screen 2. When the device 1 is returned from the MARK mode to the CALIPER mode, the mark cursor 3A will vanish from the LCD screen 2 and the readout in the readout cell 13A will be the total distance from the left cursor 3 to the right cursor 4 in its new position.

FIG. 11D shows the device 1 with LCD screen 2 as it appears in the MARK mode with the generated mark cursor 3A between the left cursor 3 and the right cursor 4. FIG. 11D also shows embossed mark 6, left hand cursor control button 7, and right hand cursor control button 8. The mark cursor 3A may be blinking.

Figure 11E:
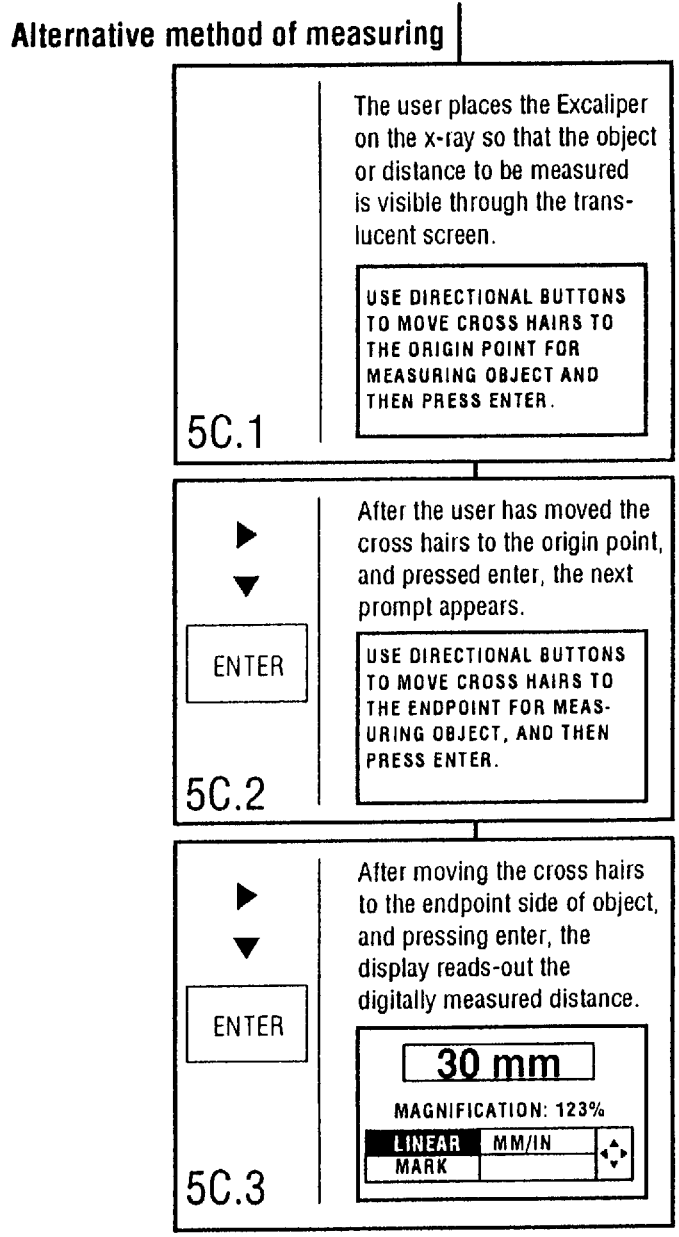
FIG. 11E shows the fourth of five flow charts explaining the operation of the Caliper Mode of the device.

FIG. 11E (consisting of sub-flow charts 5C.1, 5C.2, and 5C.3) shows the fourth of five flow charts explaining the operation of the Caliper Mode of the device. Sub-flow chart 5C.1 shows the beginning of an alternative procedure to use the device 1 to determine a linear distance once the magnification percentage is known and if LCD 2 uses pixels instead of annunciators. Instead of moving the cursor, the user moves a crosshair 20 to one side of an object seen through the transparent LCD screen 2 and presses "ENTER" on the control panel 19. This method may also be used if LCD screen is comprised of annunciators. If annunciators are used, the right hand cursor 4 would be used instead of crosshair 20.

Sub-flow chart 5C.2 shows the second step which is moving the cross-hair 20 to the other side of the object or distance to be measured and again pressing "ENTER" on the control panel 19.

Sub-flow chart 5C.3 shows that the actual distance being measured (not the distance on the radiograph for example but the actual distance represented by the X-ray image) is shown in the readout cell 13a.

Figure 11F:
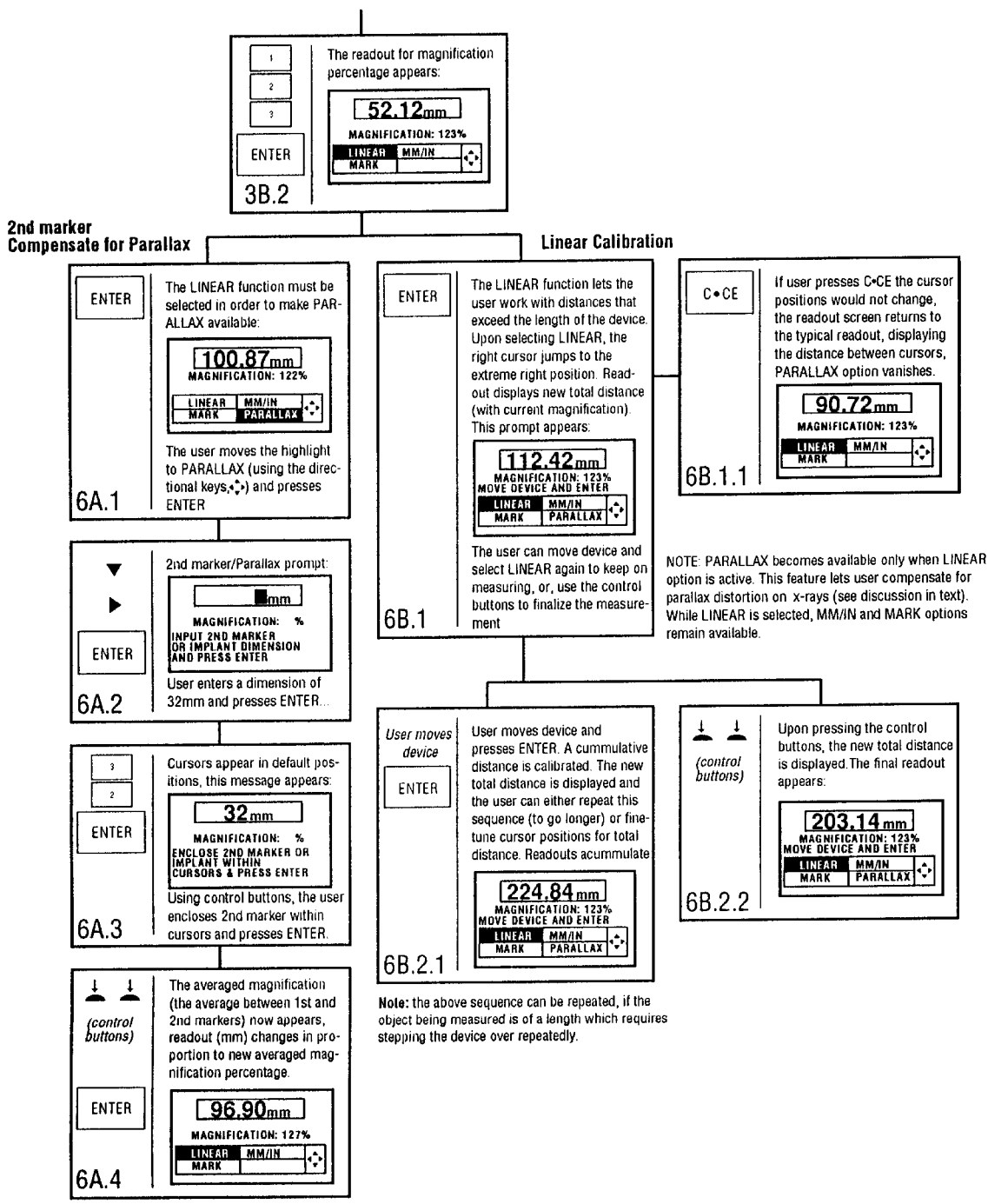
FIG. 11F shows the fifth of five flow charts explaining the operation of the Caliper Mode of the device.

FIG. 11F (consisting of sub-flow charts 6A.1, 6A.2, 6A.3, 6A.4, 6B.1, 6B.1.1 6B.2.1, 6B.2.2 and, for continuity, 3B.2) shows the fifth of five flow charts explaining the operation of the Caliper mode of the device.

A parallax error in measurement from X-ray films occurs due to the fact that different body parts may be at different distances from the unexposed X-ray film prior to exposure. For example, when making an X-ray image of a leg, the proximal portion of the femur may be farther from the unexposed X-ray film than the distal portion of the tibia because the femur is surrounded by more soft tissue than the tibia. The X-ray film records the shadow of a bone. The shadow width increases with increasing distance from the bone to the X-ray film. Thus, a correction must be made for the fact that the same width radio-opaque objects which are at different distances from an X-ray film will appear on the developed film as having different widths. Thus, a correction must be made for this parallax error. The correction, in this embodiment of the device 1, is to use as the magnification percentage for an entire radiograph, for example, the average of the magnification percentages calculated from known markers at opposite ends of the object portrayed on the radiograph. Alternative corrections could be calculated by using the arithmetic average of the magnification percentages calculated from more than two markers.

Sub-flow chart 6A.1 shows the appearance of LCD screen 13 when the PARALLAX function of the CALIPER mode has been selected. The default position of the highlight among cells 15–18 of LCD 13 is on the LINEAR cell 15. When the device 1 enters the CALIPER mode even though the highlight is on LINEAR, the LINEAR function has not been selected. To select the LINEAR function, the user must press "ENTER" on control panel 19 when the highlight is on LINEAR cell 15. The PARALLAX option appears whenever the LINEAR function is selected. With the device 1 in the CALIPER mode and with the LINEAR function selected, the user selects the PARALLAX sub-function of the LINEAR function by using the directional keys on the control panel 19 to place the movable highlight on the PARALLAX cell 18 and then pressing "ENTER" on control panel 19.

Even before entering the PARALLAX sub-function, the user has determined the magnification percentage as shown by a known marker in one position on, for example, a radiograph (as discussed in connection with FIG. 11A above).

Sub-flow chart 6A.2 shows that the next step in correcting for the parallax error is to input an actual linear measurement of a marker in a second position on, for example, a radiograph and to press "ENTER" on the control panel 19. In the example shown the actual width of the second marker is 32 mm.

Sub-flow chart 6A.3 shows that cursors appear in default positions on LCD screen 2 and directs the user to use the cursors to measure the marker distance as shown on, for example, a radiograph. The user then uses the control buttons 7 and 8 to place the lefthand cursor 3 on the left side of the second marker and the righthand cursor 4 on the right side of the second marker and presses "ENTER" on the control panel 19.

Sub-flow chart 6A.4 shows that the average magnification (the arithmetic average of the magnification needed to measure accurately the first marker and the magnification needed to measure accurately the second marker) now appears in the magnification percentage cell 14. The readout cell 13a shows the actual distance being measured which has been corrected by the average magnification percentage now shown in the magnification percentage cell 14. The device returns to the CALIPER mode and the highlight is in its default position over LINEAR cell 15. Because LINEAR is no longer an active function, the word "PARALLAX" no longer appears in PARALLAX cell 18.

Sub-flow chart 6B.1 shows how the user may measure distances which exceed the maximum distance between the cursors 3 and 4 of LCD screen 2 of device 1. The measurement is made using the LINEAR function of the CALIPER mode. The method of selecting the LINEAR function was explained above in connection with the discussion of sub-flow chart 6A.1 of FIG. 11F. Upon selecting the LINEAR function in the CALIPER mode, left cursor 3 is in the default position 5 mm to the right of the left edge of LCD screen 2 and right cursor 4 is aligned with embossed mark 6 near the extreme right edge of LCD screen 2. Readout cell 13a displays the total distance actually represented by the inter-cursor spacing at the current magnification percentage as shown in the magnification percentage cell 14.

Sub-flow chart 6B.1.1 shows that if at any time while using the LINEAR function the user presses the "C/CE" button on the numeric keypad 11, the cursor positions would not change, the readout cell 13a will display the typical readout showing the inter-cursor spacing, the device 1 will leave the LINEAR function and the light disappears from the PARALLAX option cell 18.

Sub-flow chart 6B.2.1 shows that after the first full screen measurement is taken as shown in sub-flow chart 6B.1, the user moves the device so the left cursor 3 coincides with the immediately prior position of the right cursor 4. The user then presses the ENTER button on the control panel 19 and the device 1 calculates a cumulative distance (the sum of the full length measurement as shown in sub-flow chart 6B.1 and the full length measurement as shown in sub-flow chart 6B.2.1) and displays this cumulative distance in the readout cell 13a. The user may repeat the procedure of sub-flow chart 6B.2.1 to measure even longer distances or the user may use cursor buttons 7 and 8 as discussed below with respect to sub-flow chart 6B.2.2 to measure the last segment of the total distance which last segment is a distance less than the inter-cursor spacing when the cursors are in their LINEAR mode default positions.

Sub-flow chart 6B.2.2 shows that the user may use the control button 7 to move the right cursor 4 to the left and thus measure a last segment less than the full LINEAR mode default inter-cursor spacing. When the user stops pressing cursor control button 7, device 1 displays the final distance measured in readout cell 13a, exits the LINEAR function, and returns to CALIPER mode but the final distance measured will remain in readout cell 13a. If the user wishes to change the final measurement, the user may press cursor control button 7 or 8 to move the cursor to the appropriate position. As the cursor moves, the appropriate total distance will appear in readout cell 13a. As discussed above with respect to sub-flow chart 6B.1.1, if the user wishes to restore the reading in readout cell 13a to show the full LINEAR mode default inter-cursor spacing (as opposed to the total distance which has been measured using the LINEAR function), the user presses the "C/CE" button on the numeric keypad 11, the cursor positions would not change and the readout cell 13a will display the typical readout showing the inter-cursor spacing. The inclinometer may be used to insure that the distance greater than the width of the device is measured in a straight line.

ANGLE MODE

Figure 12:
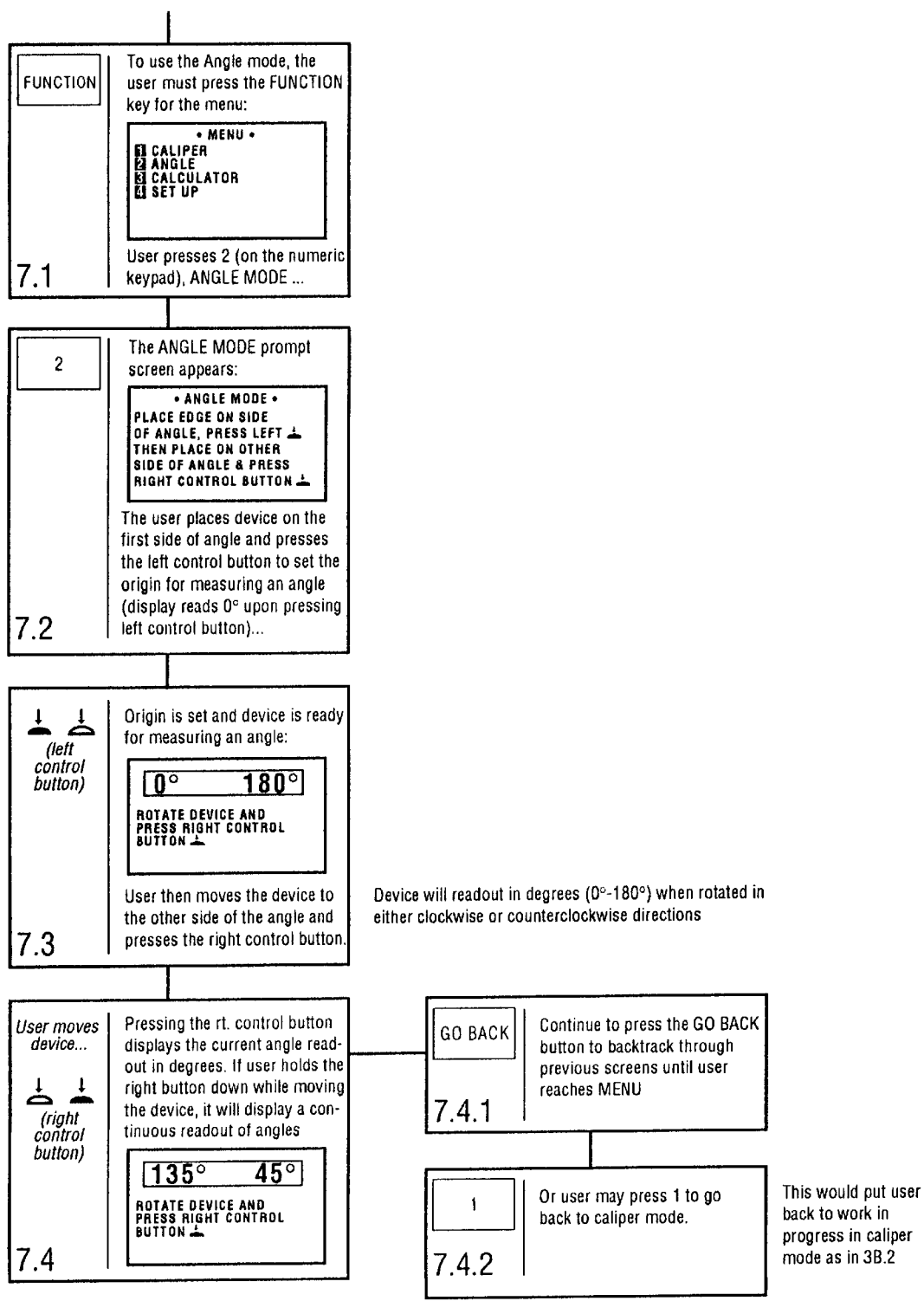
FIG. 12 shows a flow chart explaining the operation of the Angle Mode of the device.

FIG. 12 (consisting of sub-flow charts 7.1, 7.2, 7.3, 7.4, 7.4.1, and 7.4.2) shows a flow chart explaining the operation of the ANGLE mode of the device. As mentioned above, to select the ANGLE mode, the user presses the "2" key on numeric keypad 11 when the device 1 displays the main MENU.

The ANGLE mode provides the function of a goniometer which is an instrument for measuring angles. In the medical profession, a goniometer is used, for example, to measure the shaft-neck-head angle of a femur. Such a measurement can be used to determine, for example, the angle of an implant used to repair a fractured femur.

Sub-flow chart 7.1 shows that the user presses "2", on the numeric keypad 11 to select the ANGLE mode when the device 1 is displaying the main MENU on LCD screen 2.

Sub-flow chart 7.2 shows that the user begins to measure an angle by placing the horizontal scribed centerline 5 of the LCD screen 2 along one side of the angle and pressing the left control button 7 which sets the origin for measuring the angle and sets the first side of the angle.

As shown in sub-flow chart 7.3, as soon as the left control button 7 is pressed, the readout cell 13a reads 0 degrees (0°) on the left side and 180° on the right side. The user then moves the centerline of LCD screen 2 to the other side of the angle being measured and presses the right control button 8.

Sub-flow chart 7.4 shows that after moving the device 1 counterclockwise the centerline is set on the other side of the angle being measured and the right control button 8 is pressed, the current angle measurements are shown in the readout cell 13a.

If the device 1 is moved counterclockwise, the angle reading shown on the left is the angle through which the device 1 was moved. The angle reading shown on the right is the complement of the angle reading on the left of readout cell 13A. The sum of the two angles will always be 180° degrees.

If the device 1 is moved clockwise, the angle reading shown on the right is the angle through which the device 1 was moved. The angle reading shown on the left is the complement of the angle reading on the right of readout cell 13A. The sum of the two angles will always be 180° degrees.

Sub-flow chart 7.4.1 shows that by pressing the "GO BACK" button on the control panel 19, the user may return to the main MENU.

Sub-flow chart 7.4.2 shows that alternatively, the user may press "1" directly on the numeric keypad to return to work in progress in the CALIPER mode as shown in sub-flow chart 3B.2.

CALCULATOR MODE

Figure 13:
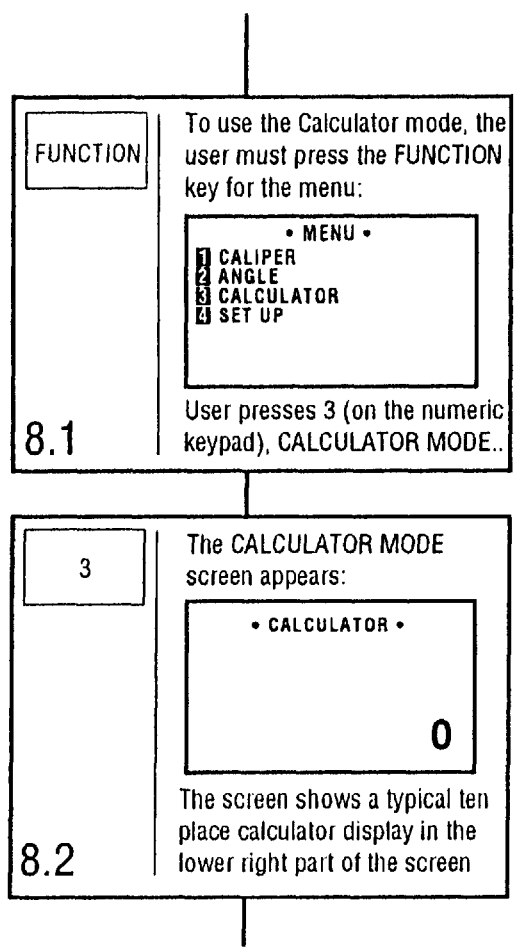
FIG. 13 shows a flow chart explaining the operation of the Calculator Mode of the device.

FIG. 13 (consisting of sub-flow charts 8.1 and 8.2) shows the single flow chart explaining the operation of the Calculator mode of the device. As mentioned above, to select the CALCULATOR mode, the user presses the "3" key on numeric keypad 11 when device 1 displays the main Menu.

Sub-flow chart 8.1 shows that the CALCULATOR mode is selected from the main MENU by pressing "3" on numeric key pad 11.

Sub-flow chart 8.2 shows that a typical ten digit calculator appears on LCD screen 13. The calculator can be controlled by using numeric keypad 11 and control panel 19 which has symbols for addition, subtraction, multiplication, and division on the directional keys on the control panel 19. In the CALCULATOR mode, the mathematical symbols are activated rather than the directional keys when the buttons are pressed. For example, in the Calculator mode, when the control panel button for upward motion is pressed, the addition function is activated. To select another function, the user presses the "FUNCTION" key on the control panel 19.

Additional features which include, but are not necessarily limited to templating, implant selection, and implant tracking may also be incorporated into the device.

IMPLANT TEMPLATING MODE

It is sometimes useful prior to an operation to place an implant in a living body to have a template of the orthopaedic device which will be implanted in a living body. Uses of the template include, but are not necessarily limited to, placing the template over a radiograph of the template's intended location to determine whether the template is of the appropriate size.

In the templating mode, the device would prompt the user to select among templates intended for implants designed to resolve problems in the hip, knee, spine, or other areas of the body (e.g., general trauma or trauma to the face). The device would then prompt the user to make appropriate measurements needed to design an appropriate template. For example, measurements of various bones in the hip area would be needed to design a template for a hip implant. The device would then prompt the user to select the appropriate type of implant (e.g., screw, pin, plate, rod, or other). The device would then prompt the user to select sizes for the previously selected type of implant. The device would then project a template on LCD 2. The template could then be hand-adjusted using the cursor and cross-hair functions of the device to locate precise features of the template at precise points on a radiograph. All necessary information could be stored in the device 1. The device 1 could then be connected to a peripheral device which would produce a transparent or other template which could be used in conjunction with a radiograph or other scan. If LCD 2 is a graphic or dot matrix LCD, then a template whose size does not exceed the size of LCD 2 may be shown on LCD 2.

Alternatively, measurements made by the device 1 could be communicated to a computer through input/output port 26. The computer using basic information (for example, template type and size) would then use one or more peripheral devices to produce a transparent template which could be placed over a radiograph of the body portion where the implant will be placed.

IMPLANT SELECTION MODE

It is necessary prior to an operation to place an implant in a living body to select the appropriate type and size of implant which will be implanted in a living body.

In the implant selection mode, the device 1 can prompt the user to provide the necessary information for patient implant matching or selection. The necessary information includes, but is not necessarily limited to the type of implant (custom or standard), the age of the living body, the weight of the living body, the lifestyle of the living body (for example, sedentary, ambulatory, very active), the general health of the living body, the bone stock index, the type of implant (for example, hip, knee, face, or spine), the material to be used (for example, plastic, metal, with cement, cementless. All of the information about available implant types can be stored in the device 1. The device 1 can be used to make measurements needed in the implant selection process.

For example, in determining the bone stock index for a hip implant is it is necessary to measure the inner and outer diameters of the femur 5 centimeters ("cm") distal to the proximal aspect of the lesser trochanter.

After all necessary measurements and information needed to select an implant is entered into the device, the device can select the appropriate type of implant and display on LCD 13 the relevant characteristics (for example, the implant manufacturer's name, the part number, size, and material) of the selected implant.

Alternatively, the device 1 may be used to make the needed anatomical measurements and the measurements may be communicated to an external computer through input/output port 26. The other necessary information (for example, implant material) could be provided from device 1 or could already be stored in or accessible to the external computer.

IMPLANT TRACKING MODE

It is useful after placing an implant in a living-body to have a record of the performance of the implant in the body and of the interaction of the body with the implant.

The Implant Tracking mode of the device can be used post-operatively to collect various data on the initial placement of an implant. The data may then be stored in the device 1 or communicated (through input/output port 26) to a computer (including, but not necessarily limited to, a personal computer) and the initial post-operative data would serve as a benchmark for future analysis of radiographic changes, such as radiolucency, osteolysis, and heterotopic bone. The necessary calculations may be made either in the device 1, in an external computer, or partially in device 1 and partially in an external computer or computers.

When the IMPLANT TRACKING MODE is selected, the device 1 prompts the user to make various anatomical measurements which are used in implant tracking. For example, with respect to a hip implant, measurements would be made of the trochanter to shoulder distance, of the acetabular angle, of the distal diameter in the anterior-posterior direction, and of the distal diameter in the medial-lateral direction. The IMPLANT TRACKING MODE may be used with respect to any type of radio-opaque implant whose performance is being tracked.

An alternative embodiment of the device 1 would allow use of just one cursor plus the embossed mark 6.

Another embodiment of the device 1 would allow use of one or more cursors to define the sides and vertex of angles which are being measured. Another embodiment of the device would allow use of a cross-hair or cross-hairs either alone or in conjunction with one or more cursors to define the sides and vertex of an angle which is being measured.

Another embodiment of the device would allow use of three or more cursors. Another embodiment of the device would allow use of more than one mark cursor.

Another embodiment of the device would allow use of a trackball or other cursor control device to move a cursor and/or a cross-hair on an LCD screen.

Another embodiment of the device would allow use of a manually positioned sliding mechanical cursor or cursors in place of LCD 2.

The foregoing sets forth only one embodiment and alternative embodiments of a measuring device. Obviously, other embodiments can be designed within the scope of this invention.

It is to be understood that while the various aspects of the invention have been described above with respect to their preferred embodiments other embodiments within the scope and spirit of this invention are possible.

For example, while not shown in the drawings which are attached to and which form a part of this application, it is possible with modifications within the scope of this invention to have a device which is not hand-held.

By way of further example of modifications within the scope of this invention, the device could be made using materials or parts other than those discussed or shown in this application.

By way of further example of modifications within the scope of this invention, the device could have a size or shape different than those discussed or shown in this application.

By way of further example of modifications within the scope of this invention, liquid crystal device 2 could be either an active matrix device or a passive matrix device.

By way of further example of modifications within the scope of this invention, the link from the input/output port to the external computer or a peripheral device could be electromagnetic radiation which is not transmitted by wire (for example, radio, microwave, or infrared).

By way of further example of modifications within the scope of this invention, the link from the input/output port to the external computer or a peripheral device could be by a means other than electromagnetic radiation (for example, ultrasound).

By way of further example of modifications within the scope of this invention, the cursors could be controlled by a joy stick, trackball, mouse (for example, but not by way of limitation, of the type used with a desktop or portable computer), or other electromechanical control means rather than the control buttons 7 and 8 or the directional keys on the control panel 19.

By way of further example of modifications within the scope of this invention, the device could have only one cursor. In this embodiment, all distance measurements would be made between a fixed point (for example, the left edge of LCD screen 2) and a movable cursor.

By way of further example of modifications within the scope of this invention, the device could have one annunciator or pixel per cursor and not a plurality of annunciators or pixels per cursor.

By way of further example of modifications within the scope of this invention, the device could have one graphic LCD instead of a primary LCD and a secondary LCD. In an embodiment with just one LCD, the measurements and prompts would be displayed on the same screen as the cursors.

By way of further example of modifications within the scope of this invention, the device could use directions on the LCD screen 13 other than those shown in the examples given above. For example, distances and angles between anatomical features other than those mentioned above could be used in various modes of the device (including, but not limited to, the IMPLANT TEMPLATE MODE, the IMPLANT SELECTION MODE, and the IMPLANT TRACKING mode).

By way of further example of modifications within the scope of this invention, the device in either a hand-held size or a larger size could be mounted on a light box of the type used to view radiographs or other scans. The controls could be either on the device or detached from the device. For example, while light boxes are usually at eye level, the cursor controls in the form of directional keys, a trackball, a joystick, a mouse, or some other control means could be mounted at hand or foot level or some other level and the cursor control means could be in communication with the cursors on the device.

By way of further example of modifications within the scope of this invention, the device could be embodied in a large transparent LCD with a touch sensitive surface or screen which would produce a virtual keyboard and appropriate keys on the screen when the proper place on the screen or an associated frame of the LCD is touched.

By way of further example of modifications within the scope of this invention, the cursor or cursors could be a mechanical cursor or cursors which could be of a type which includes, but is not limited to, manually positioned sliding mechanical cursors. For example, a mechanical cursor could be operated by a thumb wheel coupled to a mechanical linkage, a potentiometer, a shaft encoder, or some other operational or control means.

By way of further example of modifications within the scope of this invention, the electrical power could be provided to the device through an electrical cord connected to an external power source or through some other means.

The description and examples are intended to illustrate and not limit the scope of the invention which is defined by the full scope of the appended claims and which invention is entitled to protection within the full scope of the appended claims.

What is claimed is:

1. A measuring device including:
   a case,
   a transparent display mounted in the cases;
   a processor;
   means for generating and controlling at least one cursor displayed on the display;
   means for measuring distances using the at least one cursor relative to a reference in the display; and
   means for measuring a change in the angular orientation of the case using a reference in the transparent display.

2. A measuring device comprising:
   a case;
   display means mounted in the case including a transparent display for viewing objects to be measured therethrough and having a reference for positional and angular measurement therein;
   processor means secured in the case and coupled to the display for processing data inputs and providing data outputs and display outputs;
   means coupled to the processor for controlling at least one movable cursor for display on the transparent portion of the display relative to the positional reference and producing data indicative of the position of the movable cursor relative to the positional reference;
   distance measuring means associated with the processor means responsive to data indicative of the position of the cursor relative to the positional reference for producing an indication of a distance therebetween;
   angle sensor means secured in the case and coupled to the processor for sensing a change in orientation of the case using the angular reference in the transparent portion of the display and producing data indicative of the orientation thereof using said angular reference; and
   angle measuring means associated with the processor means and responsive to data indicative of the position of the angle sensor means for producing an indication of the angular orientation of the case using the angular reference.

3. The measuring device according to claim 2 wherein the transparent display comprises a liquid crystal display.

4. The measuring device according to claim 2 further including means coupled to the processor means for entering alphanumeric character data into the processor means.

5. The measuring device in accordance with claim 4 wherein the processor means includes means for producing a menu for prompting the user and for displaying said menu on the display means.

6. The measuring device in accordance with claim 2 further comprising:
   means associated with the processor means responsive to the distance measuring means for producing an indication of a ratio between the distance between the movable cursor in a first position and the positional reference on the transparent display and a number entered into the processor.

7. The measuring device of claim 6 wherein the number represents a selectable percentage of the distance.

8. A measuring device in accordance with claim 6 further including means for multiplying the ratio by a second distance between the movable cursor in a second position and the positional reference on the transparent display.

9. The measuring device in accordance with claim 2 wherein the measuring means includes means for measuring a distance greater than the width of the transparent display.

10. The measuring device in accordance with claim 2 wherein the measuring means includes means for measuring a plurality of distances and calculating the average of such distances.

11. The measuring device in accordance with claim 2 wherein the processor means includes means for performing addition, subtraction, multiplication and division.

12. The measuring device in accordance with claim 2 further including an output port; and
means for generating at the output port information for communication with an external device.

13. The measuring device of claim 12 wherein the information includes one of implant template data and implant tracking data.

14. The measuring device of claim 12 wherein the output part includes at least one of a wireless and wired link.

15. The measuring device of claim 2 further including an input port for receiving information.

16. The measuring device of claim 12 wherein the input port includes at least one of a wireless and wired link.

17. The measuring device in accordance with claim 2 further including storage means for storing implant data and means for selecting an implant from data stored in the said storage means.

18. The measuring device of claim 2 further including memory means coupled to the processor for storing data.

19. The measuring device in accordance with claim 2 further including means for collecting, storing and analyzing implant tracking information.

20. The measuring device in accordance with claim 2 wherein the positional reference comprises a fixed point on the transparent display.

21. The measuring device of claim 2 wherein the positional reference comprises a second movable cursor.

22. The measuring device according to claim 2 wherein the case includes a surface transverse to the transparent display, and wherein the means for controlling the at least one movable cursor is located on said surface for facilitating manual activation.

23. The measuring device of claim 2 wherein the case includes surface portions mounted transverse to the transparent display for facilitating manual handling over an image of the object to be measured.

24. The measuring device according to claim 2 wherein the case has a front and rear side and a photocell mounted in a rear side thereof.

25. The measuring device according to claim 24 wherein the photocell is coupled to the processor for providing power for said processor.

26. The measuring device in accordance with claim 2 further including means for controlling a second movable cursor for positioning between the positional reference and the at least one movable cursor.

27. The measuring device in accordance with claim 2 further including means for controlling a second movable cursor for positioning halfway between the positional reference and the at least one movable cursor.

28. The measuring device in accordance with claim 2 wherein the display means includes a data display for displaying at least one of alphanumerical characters, distances, angles, control information, and menu items.

29. The measuring device according to claim 2 further including means for storing a program in the processor, said program including means for prompting a user for selective operation of the program in accordance with a menu.

30. The measuring device of claim 2 wherein the display has a resolution of at least 0.3 mm.

31. The measuring device of claim 2 wherein the resolution is about 0.3 mm.

32. The measuring device of claim 2 including means for measuring values of dimensions of a plurality of representations of objects having known values of dimensions;
means for comparing the measured value of the dimension of each of the plurality of representations of objects with the known value of the dimension and obtaining a ratio between the measured value and the known value; and
means for averaging the ratios of the plurality of representations of objects to obtain an average ratio used in measuring distances.

33. A measuring device comprising:
a case;
display means mounted on the case including a transparent display and a data display, said transparent display for viewing-objects to be measured therethrough, said data display for selectively displaying a menu of at least one of a plurality of functions;
processor means secured in the case and coupled to the display;
storage means coupled to the processor for storing a program including said plurality of functions and corresponding menu items for displaying selected ones of the functions on said display means; and
means coupled to the processor for allowing a user to select the at least one of said functions from the menu.

34. The measuring device according to claim 33 wherein the functions include at least one of control, positional, angular, template, ratio, implant tracking and centering functions respectively.

35. The measuring device according to claim 34 wherein the display includes a transparent portion having measurement references therein and for viewing objects to be measured therethrough relative to measurement references.

36. The measuring device of claim 34 including means for operating the processor to perform the at least one of the control functions.

37. The measuring device according to claim 33 wherein the case includes a surface transverse to the display and wherein the means for controlling the at least one movable cursor is located on said surface for facilitating manual activation.

38. The measuring device of claim 33 wherein the case includes surface portions mounted transverse to the display for facilitating manual handling over an image of the object to be measured.

39. The measuring device of claim 38 wherein the device is hand held.

40. A measuring device comprising:
a case;
a processor for performing control and data functions;
transparent display means coupled to the processor and mounted in the case including a positional and angular reference and data display means for displaying a menu of said control and data functions;
means for selecting from the menu the control and data functions to be performed by the processor;
means coupled to the processor for entering data therein;
means for controlling at least one movable cursor for display on the transparent display relative to the positional reference; and angle sensor means secured in the case for sensing a change in orientation of the case using the angular reference.

41. The measuring device of claim 1 including means for measuring values of dimensions of a plurality of representations of objects having known values of the dimensions;

means for comparing the measured value of the dimension for each of the plurality of representations of objects with the known value of the dimension and obtaining a ratio between the measured value and the known value; and means for averaging the magnification ratios for the plurality of representations of objects to obtain an average magnification ratio used in measuring the distances.

\* \* \* \* \*